(12) United States Patent
Dwork

(10) Patent No.: US 11,523,904 B2
(45) Date of Patent: Dec. 13, 2022

(54) SYSTEM FOR LOADING A TRANSCATHETER VALVE PROSTHESIS INTO A DELIVERY CATHETER

(71) Applicant: MEDTRONIC VASCULAR, INC., Santa Rosa, CA (US)

(72) Inventor: Joshua Dwork, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 395 days.

(21) Appl. No.: 16/889,146

(22) Filed: Jun. 1, 2020

(65) Prior Publication Data
US 2020/0297519 A1    Sep. 24, 2020

Related U.S. Application Data

(63) Continuation of application No. 15/478,442, filed on Apr. 4, 2017, now Pat. No. 10,667,934.

(51) Int. Cl.
*A61F 2/24*    (2006.01)
*A61F 2/966*    (2013.01)
*A61F 2/95*    (2013.01)

(52) U.S. Cl.
CPC .......... *A61F 2/2436* (2013.01); *A61F 2/2439* (2013.01); *A61F 2/966* (2013.01); *A61F 2/9522* (2020.05); *A61F 2002/9665* (2013.01)

(58) Field of Classification Search
CPC .................. A61F 2/2436; A61F 2/2439; A61F 2002/9522; A61F 2/24; A61F 2/95; A61F 2/966; A61F 2/9665
See application file for complete search history.

(56) References Cited

U.S. PATENT DOCUMENTS

| 8,226,710 | B2 | 7/2012 | Nguyen et al. |
| 2010/0049313 | A1 | 2/2010 | Alon et al. |
| 2013/0152659 | A1 | 6/2013 | Maimon et al. |

(Continued)

FOREIGN PATENT DOCUMENTS

| CN | 104968300 A | 10/2015 |
| WO | 2013/177684 A1 | 12/2013 |

(Continued)

OTHER PUBLICATIONS

Notice of First Office Action, China Application No. 201880019549.1, dated Apr. 9, 2021.

(Continued)

*Primary Examiner* — George J Ulsh
(74) *Attorney, Agent, or Firm* — Medler Ferro Woodhouse & Mills PLLC

(57) ABSTRACT

A tool for use in loading a transcatheter valve prosthesis within a delivery catheter includes a body portion, a pivotable element and a biasing element. The body portion includes a central passageway extending form a proximal end to a distal end of the body portion. The central passageway is configured to receive a distal portion of a delivery catheter therethrough. The pivotable element is attached to the body portion and is configured to secure a tether during loading of a transcatheter valve prosthesis within the delivery catheter. The biasing element compresses the pivotable element against the body portion such that the pivotable element holds a second end against the delivery catheter and secures the tether thereto. The pivotable element may be two or more pivotable elements.

19 Claims, 37 Drawing Sheets

(56) References Cited

U.S. PATENT DOCUMENTS

| | | |
|---|---|---|
| 2013/0296999 A1 | 11/2013 | Burriesci et al. |
| 2014/0144000 A1 | 5/2014 | Creavan et al. |
| 2014/0155990 A1 | 6/2014 | Nyuli et al. |
| 2014/0276408 A1 | 9/2014 | Abbate |
| 2015/0112430 A1 | 4/2015 | Creaven et al. |
| 2015/0366665 A1 | 12/2015 | Lombardi et al. |
| 2017/0042676 A1 | 2/2017 | Backus et al. |

FOREIGN PATENT DOCUMENTS

| | | |
|---|---|---|
| WO | 2016/133950 A1 | 8/2016 |
| WO | 2018/187196 A1 | 10/2018 |

OTHER PUBLICATIONS

Written Opinion of the ISA, PCT/US2018/025638, dated Jun. 28, 2018.

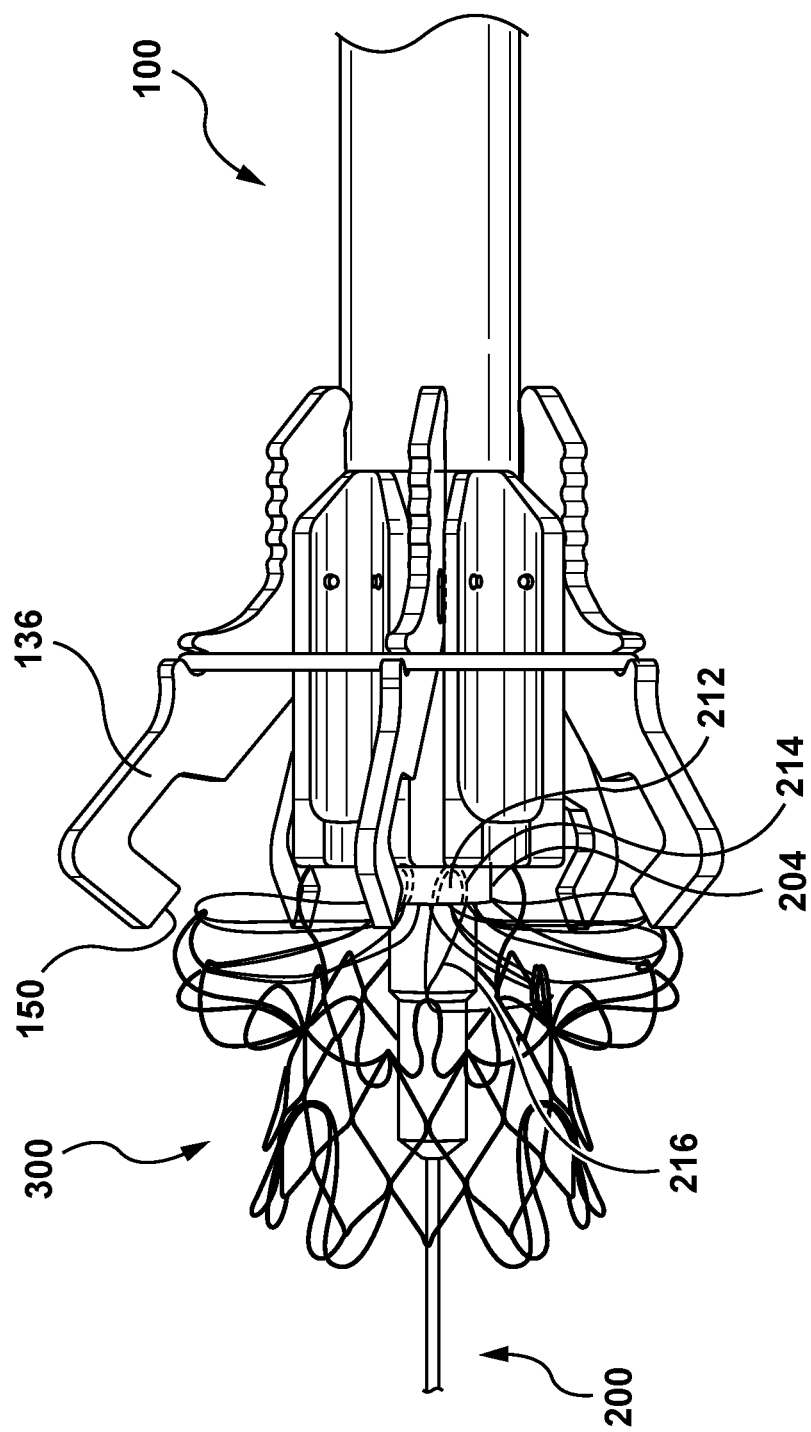

SYSTEM FOR LOADING A TRANSCATHETER VALVE PROSTHESIS INTO A DELIVERY CATHETER

CROSS-REFERENCE TO RELATED APPLICATIONS

This application is a continuation of U.S. patent application Ser. No. 15/478,442, filed Apr. 4, 2017, the contents of which are incorporated by reference herein in their entirety.

FIELD OF THE INVENTION

Embodiments hereof relate to prosthetic heart valves and methods for loading the prosthetic heart valve within a delivery catheter. More specifically, the invention relates to a system including a loading tool, and methods for loading the prosthetic heart valve into the delivery catheter.

BACKGROUND OF THE INVENTION

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement via surgical procedure is performed for patients suffering from valve regurgitation or stenotic calcification of the leaflets. Conventionally, the vast majority of valve replacements entail a full sternotomy and placing the patient on cardiopulmonary bypass. Traditional open surgery inflicts significant patient trauma and discomfort, requires extensive recuperation times, and may result in life-threatening complications.

To address these concerns, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a prosthetic heart valve, also known as a valve prosthesis, a valve stent, or a stented valve, is compacted for delivery in a catheter and then advanced, for example through an opening in the femoral artery and through the descending aorta to the heart, where the prosthesis is then deployed in the valve annulus (e.g., the aortic valve annulus).

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. In order to prepare such a prosthetic heart valve for percutaneous implantation, one type of prosthetic heart valve can include a stent frame made of a self-expanding material. With these systems, the prosthetic heart valve is crimped down to a desired size and held in that compressed state within a capsule or sheath of a delivery catheter, for example. Loading the prosthetic heart valve into the capsule of the delivery catheter is generally accomplished manually and can be difficult and time consuming. In an example, the delivery catheter may include a plurality of tethers, with a looped end of each tether threaded or woven through a respective portion of the frame of the prosthetic heart valve. Each looped end is looped around a tether post of the delivery catheter. Once the looped end of each of the plurality of tethers are looped through the frame of the prosthetic heart valve and the respective tether post, the looped ends must be held in place as the delivery catheter is manipulated such that tether posts, and releasably coupled prosthetic heart valve is loaded into the capsule and retained therein. However, manually holding the looped ends of the plurality of tethers for proper retraction and loading into the delivery catheter is difficult and time consuming.

Accordingly, there is a need for systems, tools and methods for quickly and easily loading a prosthetic heart valve into a delivery catheter.

BRIEF SUMMARY OF THE INVENTION

Embodiments hereof are related to a tool for loading a transcatheter valve prosthesis within a delivery catheter. The tool includes a body portion, a pivotable element and a biasing element. The body portion includes a central passageway extending from a proximal end to a distal end of the body portion. The body portion is configured to slidably receive the delivery catheter therein. The pivotable element is attached to the body portion. The pivotable element is configured to secure a tether during loading of the transcatheter valve prosthesis within the delivery catheter. The biasing element compresses the pivotably element against the body portion. The biased pivotable element is configured to hold a second end of the pivotable element against the delivery catheter, securing the tether during loading of the valve prosthesis.

Embodiments hereof are also directed to a system for loading a stent within a delivery catheter. The system includes a delivery catheter and a loading tool. The delivery catheter has a tether for attaching the stent to the delivery catheter during loading. The loading tool has a pivotable element. The loading tool is configured to slide onto the delivery catheter. The pivotable element is further configured to secure a looped end of the tether against the delivery catheter during loading of the stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 12 is a perspective illustration of the plurality of tethers trapped by the outer sheath of the delivery catheter of FIG. 6A.

DETAILED DESCRIPTION OF THE INVENTION

Figure 1:
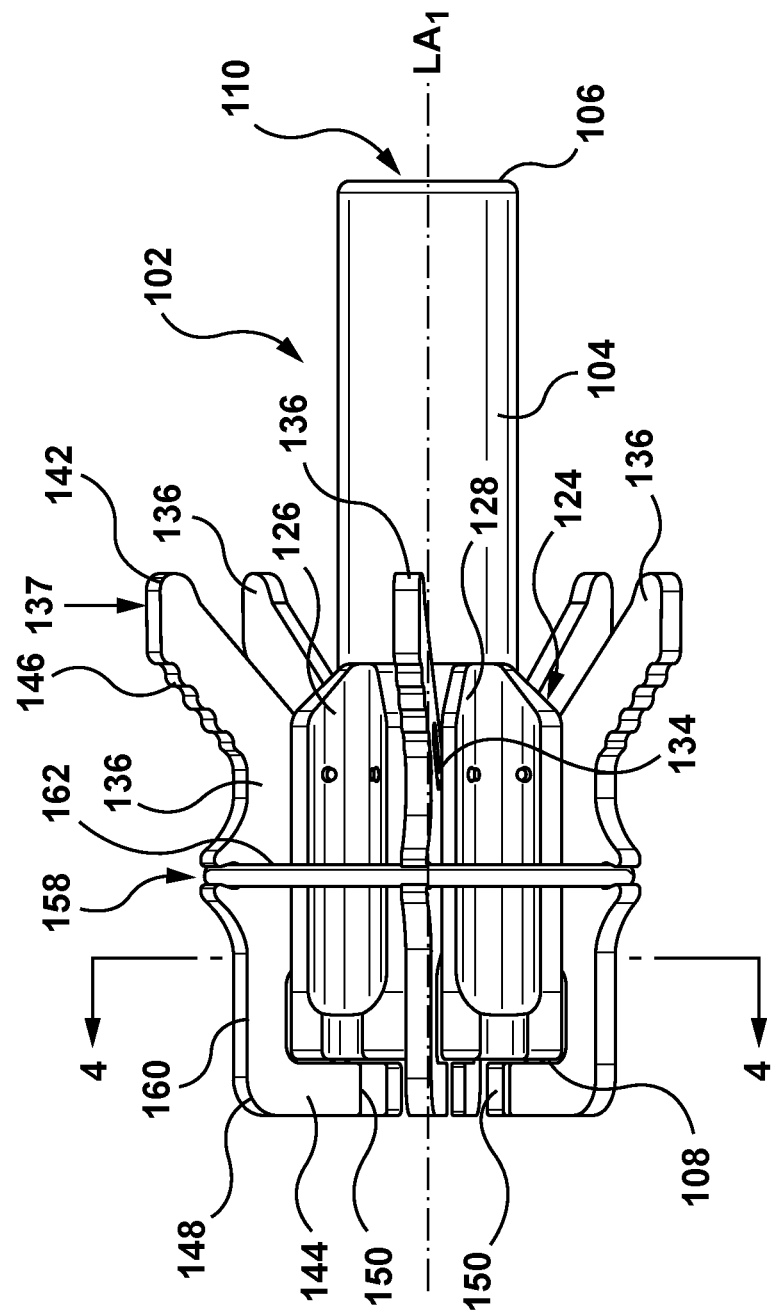
FIG. 1 is a perspective illustration of a loading tool in accordance with an embodiment hereof, in a closed configuration

Specific embodiments of the present invention are now described with reference to the figures, wherein like reference numbers indicate identical or functionally similar elements. The terms "distal" and "proximal" when used in the following description to refer to a loading tool, a catheter or delivery catheter are with respect to a position or direction relative to the treating clinician. Thus, "distal" and "distally" refer to positions distant from or in a direction away from the clinician and "proximal" and "proximally" refer to positions near or in a direction toward the clinician. When the terms "distal" and "proximal" are used in the following description to refer to a device to be implanted into a vessel, such as a prosthetic heart valve, they are used with reference to the direction of blood flow. Thus, "distal" and "distally" refer to positions downstream in the direction of blood flow and "proximal" and "proximally" refer to positions upstream in the direction of blood flow.

Heart valve prostheses (hereafter referred to as a "valve prostheses" for sake of simplicity) for use with and/or forming a part of the various transcatheter systems, devices and methods described herein may assume a wide variety of different configurations, and can be specifically configured for replacing any of the four native heart valves of the human heart. Thus, a valve prosthesis useful with the systems, devices, and methods hereof may generally be used for replacement of a native aortic, mitral, pulmonic or tricuspid valve, or to replace a failed valve prosthesis, such as one that may have been previously implanted in the native aortic or mitral valve, for example.

In general terms, such a valve prosthesis includes a frame (stent) defining an internal area within which a valve body portion having two or more valve leaflets (tissue or synthetic) is secured. The frame of the valve prosthesis has an expanded or deployed configuration that corresponds with implantation at a particular target site within the heart, and a compressed or delivery configuration when loaded within a delivery catheter, also known as a catheter-based delivery device, or delivery device, for delivery to a particular target site within the heart. Generally, each frame is a support structure that comprises a number of struts or wire segments arranged relative to each other to provide desired properties to the valve prosthesis, such as compressibility and strength.

The frame may be constructed to self-deploy or self-expand from the compressed configuration to the expanded configuration when released from the delivery catheter. The term "self-expand" and other forms thereof are used in the following description and are intended to convey that the frame structure of a valve prosthesis used in embodiments hereof is shaped or formed from a material that can be provided with a mechanical memory to return the frame structure from a compressed (delivery) configuration to an expanded (deployed) configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold frame by thermal treatment to achieve a spring temper in stainless steel, for example, or to set a shape memory in a susceptible metal alloy, such as Nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers. As an example, a valve prosthesis of the current disclosure may be similar to the Medtronic CoreValve® transcatheter aortic valve replacement valve prosthesis and as described in U.S. Pat. No. 8,226,710 to Nguyen, which is incorporated by reference herein in its entirety.

FIGS. 1-14 illustrate a system 100 and a method for loading a transcatheter valve prosthesis (hereafter referred to as a "valve prosthesis" for sake of simplicity) into a delivery catheter in accordance with an embodiment hereof. The system 100 includes a loading tool 102 (hereafter referred to as "tool 102" for sake of simplicity) and a delivery catheter 200. The system 100 further includes a loading configuration wherein the delivery catheter 200 is received within a central passageway 110 of the tool 102 for loading of a valve prosthesis therein, and a delivery configuration wherein the delivery catheter 200 is not received within the tool 102. The system 100 is configured such that when the system 100 is in the loading configuration, the loading tool 102 assists in loading the valve prosthesis into the delivery catheter 200, as described in greater detail below.

In an embodiment, as shown in FIGS. 1-5, the tool 102 includes a body portion 104, a plurality of pivotable elements 136, and a biasing element 162, as shown in FIG. 1. The body portion 104 of the tool 102 includes a proximal end 106, a distal end 108 and an inner surface defining the central passageway 110 extending distally from the proximal end 106 to the distal end 108. The central passageway 110 is an opening (bore or lumen) extending through the entirety of the longitudinal center of the body portion 104 along a first longitudinal axis LA1. The body portion 104 is sized and configured to slidably receive a distal portion of the delivery catheter 200 therethrough. When the tool 102 is positioned over the distal portion of the delivery catheter 200, the body portion 104 is further configured to assist in loading a valve prosthesis 300 into the delivery catheter 200.

Figure 3A:
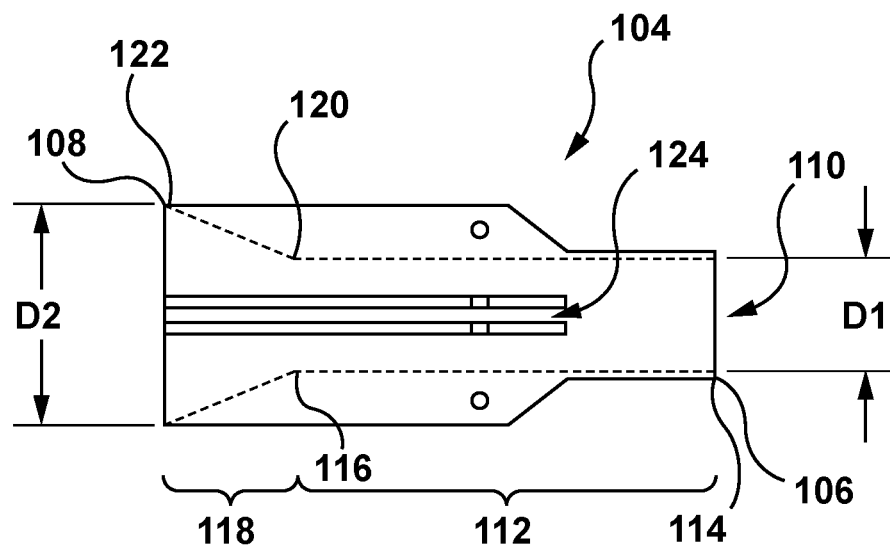
FIG. 3A is a side illustration of a body portion of the loading tool of FIG. 1 in accordance with an embodiment hereof.

In an embodiment shown in FIG. 3A, the central passageway 110 (shown as the dotted line) of the body portion 104 includes a first portion 112 and a tapered portion 118. The first portion 112 extends distally from a proximal end 114 co-located with the proximal end 106 of the body portion 104 to a distal end 116, proximal of the distal end 108 of the body portion 104. The first portion 112 is of a generally cylindrical shape and of a consistent first diameter D1. The tapered portion 118 of the central passageway 110 extends from a proximal end 120 coupled to the distal end 116 of the first portion 112 distally to a distal end 122 co-located with the distal end 108 of the body portion 104. The tapered portion 118 flares radially outwards from the proximal end 120 with the first diameter D1 to the distal end 122 with a second diameter D2, wherein the second diameter D2 is greater than the first diameter D1. Thus, the tapered portion 118 is of a general conical shape with the larger, second diameter D2 adjacent the distal end 108 of the body portion 104 tapering down (reducing diameter) proximally to the proximal end 120 at the co-located distal end 116 of the first portion 112. The tapered portion 118 is configured to compress the valve prosthesis during loading into the delivery catheter 200. The conical shape of the tapered portion 118 of the central passageway 110 is configured to ease (facilitate) radial compression of the valve prosthesis as the valve prosthesis is loaded into the delivery catheter 200. In another embodiment, shown in FIG. 3B, the body portion 104 includes a central passageway 110' extending from a proximal end 106' to a distal end 108'. The central passageway 110' is a generally tubular shape that is of a consistent diameter D3. The body portion 104 may be formed of metal and/or polymeric material such as, but not limited to polyethylene, PEBA, polyamide and/or combinations thereof. The body portion 104 may be formed by various methods, non-limiting examples of which include machining, extrusion, molding, or other methods and combinations of methods.

Figure 2A:
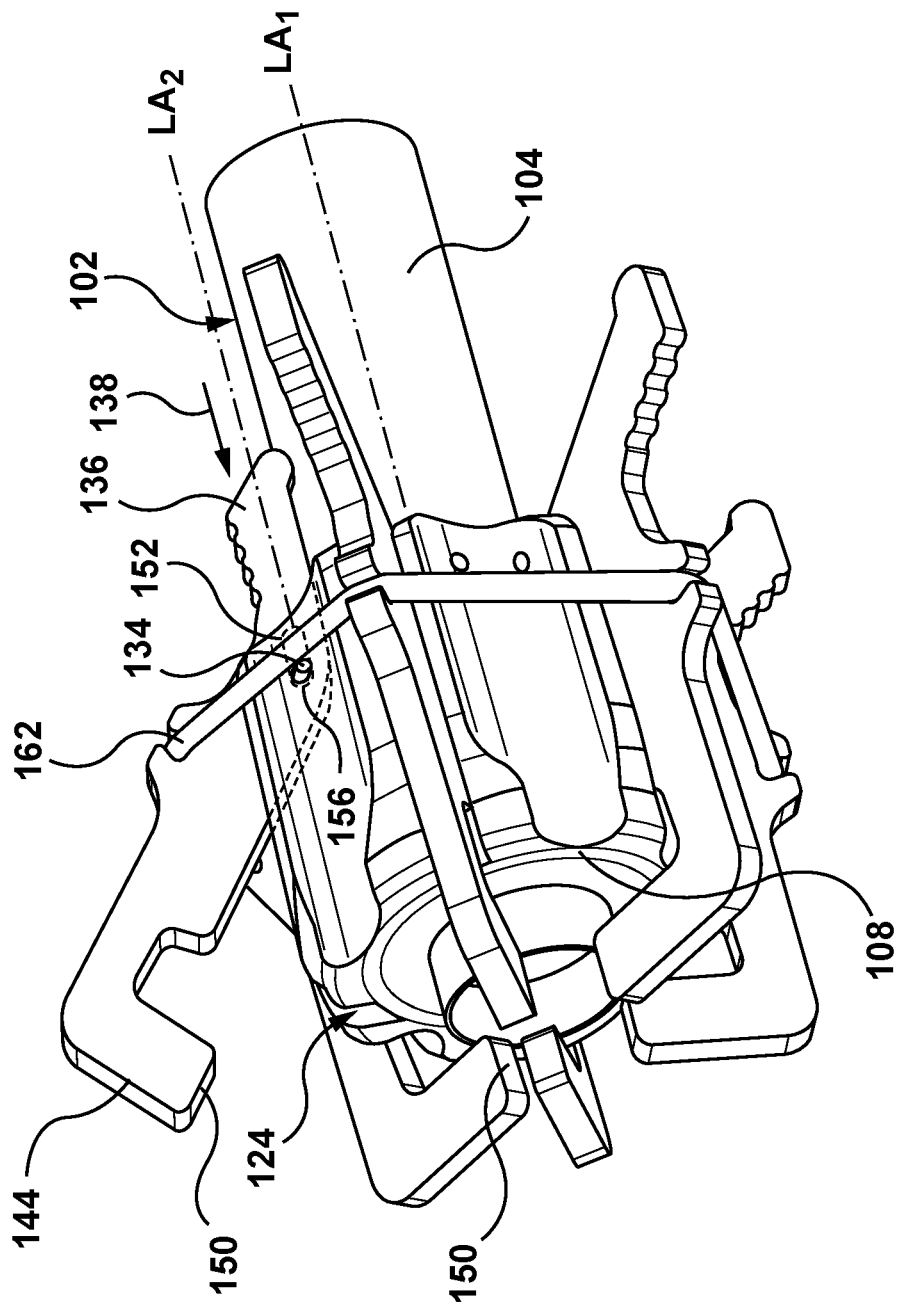
FIG. 2A is a perspective illustration of the loading tool of FIG. 1 in a second configuration.
Figure 3B:
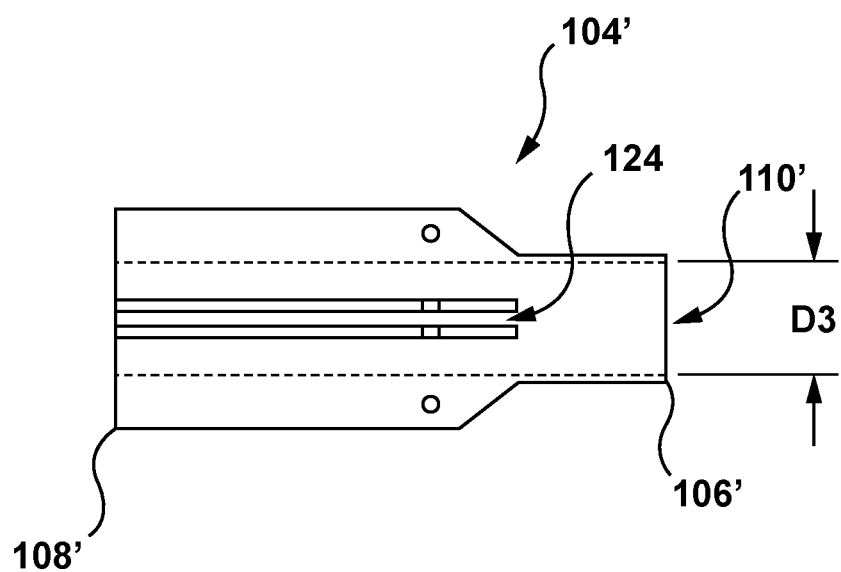
FIG. 3B is a side illustration of a body portion of the loading tool of FIG. 1 according to another embodiment hereof.
Figure 4:
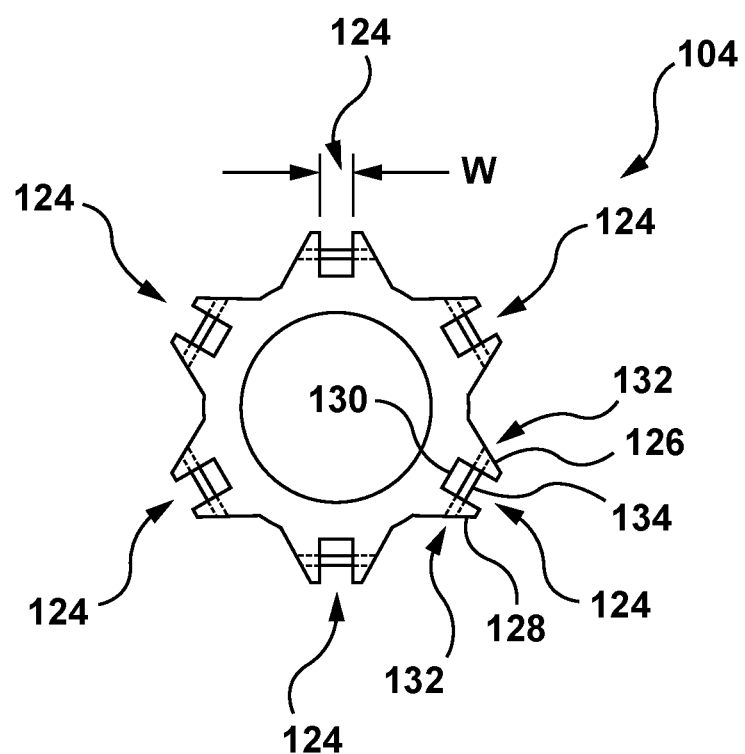
FIG. 4 is a cross-sectional illustration of the body portion of the loading tool of FIG. 1 taken along line 4-4 in accordance with an embodiment hereof.

The body portion 104 further includes a plurality of pivotable element slots 124 (FIG. 4). Each pivotable element slot 124 is a channel or recess defined within an outer surface of the body portion 104. In an embodiment, each pivotable element slot 124 is defined by a first wall 126, a second wall 128, and a recessed surface 130, as shown in FIG. 4. The first and second walls 126, 128 extend generally radially outward from the outer surface of the body portion 104, generally perpendicular to the first longitudinal axis LA1. The facing surfaces of the corresponding first and second walls 126, 128 are generally parallel to each other and extend longitudinally along the body portion 104 from the distal end 108 (FIG. 1) extending proximally to a location distal of the proximal end 106 (FIG. 1). A width W of each pivotable element slot 124 is sized to pivotably receive the corresponding pivotable element 136 (FIG. 1) therein. Each pivotable element slot 124 includes a pivot bore 132. In an embodiment, the pivot bore 132 extends transversely to the pivotable element slot 124 and through corresponding first and second walls 126, 128, as shown in FIG. 4. Each pivot bore 132 is configured to receive a pivot 134 therethrough, such that the pivot 134 extends through the first wall 126, the corresponding pivotable element 136 (not shown in FIG. 4 for clarity), and the corresponding second wall 128. The pivot 134 is configured such that the corresponding pivotable element 136 (FIG. 1) is pivotable about the pivot 134. Thus, the pivot 134 couples the corresponding pivotable element 136 within the corresponding pivotable element slot 124 and is the pivot point about which the corresponding pivotable element 136 may pivot, as shown in FIG. 2A. In an embodiment, the pivot 134 is a pin or shaft. While the embodiment of FIGS. 1-4 show the body portion 104 with six (6) pivotable element slots 124, it is understood that more or fewer pivotable element slots 124 and corresponding pivotable elements 136 may be provided, depending on the application. Moreover, while the pivotable element slots 124 and the corresponding pivotable elements 136 are shown spaced equally about a perimeter of the tool 102, this is not meant to limit the design and the pivotable element slots 124 and the corresponding pivotable elements 136 may not be equally spaced about the perimeter of the tool 102.

Figure 5:
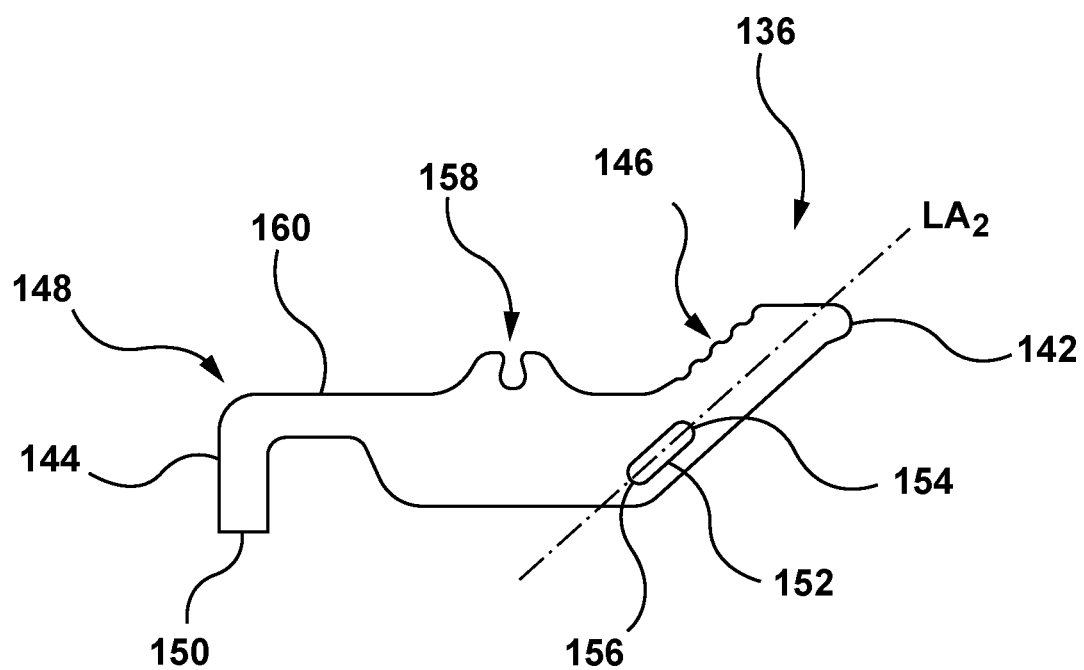
FIG. 5 is a side illustration of a pivotable element of the loading tool of FIG. 1.

The tool 102 includes the plurality of pivotable elements 136, as shown in FIG. 1. FIG. 5 shows in greater detail one of the pivotable elements 136. Each pivotable element 136 is configured to secure a corresponding tether of the delivery catheter during loading of the valve prosthesis into the delivery catheter, as described in greater detail below. Each pivotable element 136 includes a first end 142 and a second end 144. The first end 142 is towards the proximal end 106 of the body portion 104 and the second end 144 is adjacent the distal end 108 of the body portion 104. In an embodiment, the second end 144 of each pivotable element 136 extends distally beyond the distal end 108 of the body portion 104. Each pivotable element 136 extends longitudinally along the outer surface of the body portion 104 at least partially within the corresponding pivotable element slot 124. Each pivotable element 136 is pivotably coupled to the body portion 104 by the corresponding pivot 134, as previously described. In an embodiment, each pivotable element 136 further includes a bend 148 and a contact surface 150 at the second end 144. The bend 148 is configured such that the second end 144 of the pivotable element 136 is curved radially inward towards the first longitudinal axis LA1 of the body portion 104 distal of the distal end 108 of the body portion 104, as shown in FIG. 1. More specifically, the bend 148 is configured such that the contact surface 150 at the second end 144 of each pivotable element 136 is aligned generally parallel to the first longitudinal axis LA1 when each pivotable element 136 is in a first (closed) configuration, as shown in FIG. 1. In an embodiment, the second end 144 of each pivotable element 136 is biased towards the first longitudinal axis LA1 by the biasing element 162 (FIG. 1), described below. Thus, when each pivotable element 136 is in the first (closed) configuration, the respective contact surface 150 of each pivotable element 136 is biased towards the first longitudinal axis LA1 of the tool 102. Moreover, when each pivotable element 136 is in a second (open) configuration, described in greater detail below, the second end 144 of the respective pivotable element 136 is disposed radially outward from the distal end 108 of the body portion 104 of the tool 102, as shown in FIG. 2A.

Figure 2B:
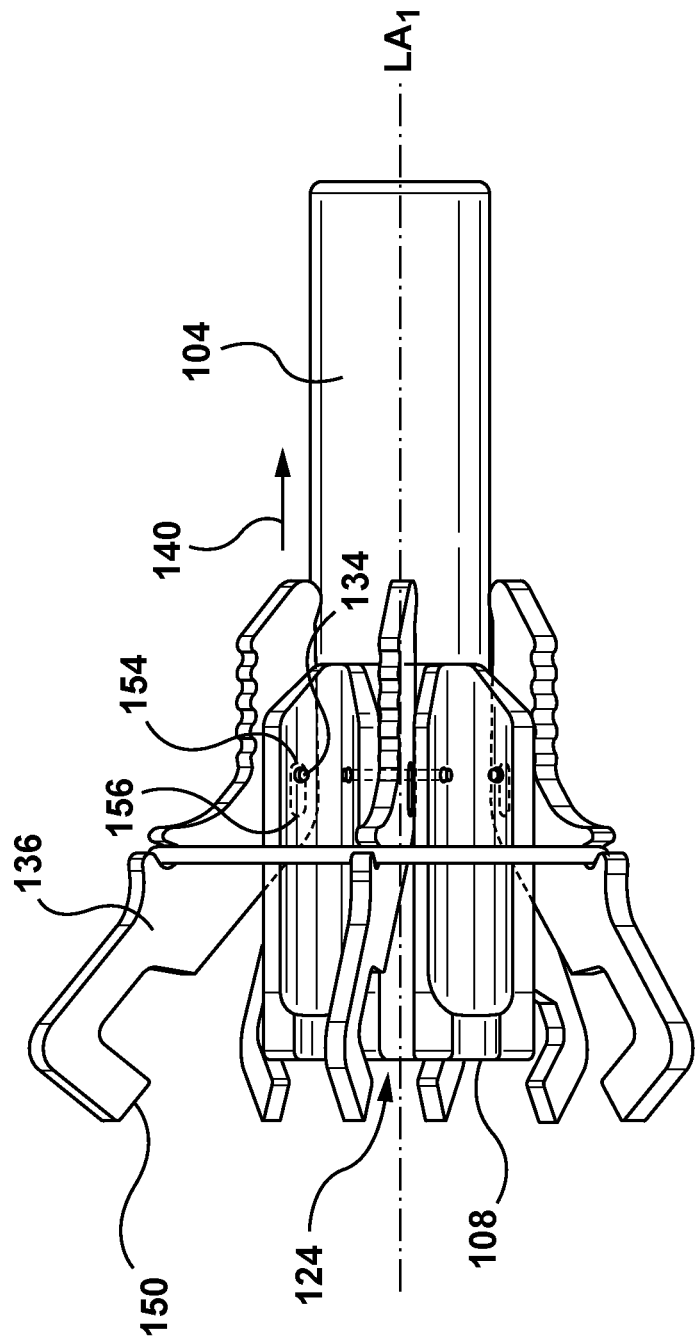
FIG. 2B is a perspective illustration of the loading tool of FIG. 1 in a third configuration.

In an embodiment, each pivotable element 136 further includes a pivot slot 152, as shown in FIG. 2A and in greater detail in FIG. 5. In an embodiment, each pivot slot 152 is an oval aperture extending transversely through a body portion of the pivotable element 136. When the pivotable element 136 is coupled to the body portion 104, the pivotable slot 152 is aligned with the corresponding pivot bore 132. The pivot slot 152 is aligned with the pivot bore 132 such that the corresponding pivot 134 may be disposed therethrough. The pivot slot 152 is configured such that the pivotable element 136 may pivot about the corresponding pivot 134. The pivot slot 152 includes a first (proximal) end 154 and a second (distal) end 156. The pivot slot 152 includes a second longitudinal axis LA2 aligned generally parallel to the first longitudinal axis LA1 of the body portion 104 when the pivotable element 136 is in the second configuration (FIG. 2A) or a third (locked open) configuration (FIG. 2B). When in the second configuration or the third configuration, the pivot slot 152 is slidable or translatable relative to the pivot 134 and thus the corresponding pivotable element 136 is slidable or translatable relative to the body portion 104, as described below.

In an embodiment, each pivotable element 136 further includes an actuator surface 146, as shown in FIG. 1 and in greater detail in FIG. 5. Each actuator surface 146 is configured for user manipulation to pivot the corresponding pivotable element 136 about the corresponding pivot 134. In an embodiment, each actuator surface 146 is disposed adjacent to the corresponding first end 142 of the pivotable element 136. Each actuator surface 146 is a surface facing radially outward from the first longitudinal axis LA1 of the body portion 104. Each actuator surface 146 may include a texture thereon to assist in manipulation of the pivotable element 136. While the actuator surface 146 is described herein as disposed adjacent to the first end 142 of the pivotable element 136, this is not meant to limit the design, and the actuator surface 146 may be disposed in other locations suitable for the purposes described herein.

In an embodiment, each pivotable element 136 further includes a biasing slot 158 on an outer surface 160 of each pivotable element 136, as shown in FIG. 1 and in greater detail in FIG. 5. The biasing slot 158 is disposed between the first end 142 and the second end 144 of each pivotable element 136. The outer surface 160 described herein is the surface of the pivotable element 136 facing radially outward from the first longitudinal axis LA1 of the body portion 104. Each biasing slot 158 is sized and configured to receive the biasing element 162 therein such that the biasing element 162 biases the second end 144 towards the first longitudinal axis LA1. Each biasing slot 158 may be formed as an integral component of the pivotable element 136 by methods including, but not limited to casting, machining, or other methods suitable for the purposes described herein.

In an embodiment, each pivotable element 136 may be situated relative to the body portion 104 in a first or closed configuration (FIG. 1), a second or open configuration (FIG. 2A) and the third or locked open configuration (FIG. 2B). Alternatively, in other embodiments, each pivotable element 136 may include only the first and the second configurations. In the first configuration, the contact surface 150 of the respective pivotable element 136 is substantially parallel to the first longitudinal axis LA1 of the loading tool 102 and biased thereto, as shown in FIG. 1. Moreover, when in the first configuration, the pivot 134 is disposed at the second (distal) end 156 of the pivot slot 152. In addition, when the pivotable element 136 is in the first configuration and the system 100 is in the loading configuration, the contact surface 150 of the pivotable element 136 is configured to contact an outer surface of the delivery catheter 200 and secure a tether of the delivery catheter during loading of the valve prosthesis 300 therein, as described in greater detail below. In the second configuration, the contact surface 150 of the respective pivotable element 136 is disposed radially outward from the body portion 104 (FIG. 2A) and does not contact an outer surface of the delivery catheter 200 when the system 100 is in the loading configuration. Further, when the pivotable element 136 is in the second configuration, the pivot 134 is disposed at the second (distal) end 156 of the pivot slot 152 such that the pivotable element is biased to return to the first configuration by the biasing element 162. In the third configuration, the pivotable element 136 is slid or translated distally within the corresponding pivotable element slot 124 and relative to the body portion 104 and locked into the third configuration. In the third configuration, the contact surface 150 of the respective pivotable element 136 disposed radially outward from the body portion 104 (FIG. 2B) and does not contact the outer surface of the delivery catheter 200 when the system 100 is in the loading configuration. Further, when the pivotable element 136 is in the third configuration, the pivot 134 is disposed at the first (proximal) end 154 of the pivot slot 152. With the pivot 134 disposed at the first (proximal) end 154 of the pivot slot 152, and the first end 142 of the pivotable element 136 pushed towards the longitudinal axis LA1, the center of rotation of the pivotable element has been shifted such that the biasing element 162 biases the pivotable element 126 towards the third configuration. This allows the pivotable element 136 to remain open without pressure applied to the surface 146. Each pivotable element 136 may be transitioned from the first configuration to the second configuration by user application of inward radial force to a proximal portion of the pivotable element. Each pivotable element 136 may be transitioned from the second configuration to the third configuration by user application of a distal longitudinal force to the pivotable element 136.

As shown in FIG. 1, the tool 102 further includes the biasing element 162. In general, the biasing element 162 applies an inward radial force on each pivotable element 136. In an embodiment, the biasing element 162 is an elastic band which encircles (circumferentially surrounds) the plurality of pivotable elements 136 and is received within the corresponding biasing slot 158 of each pivotable element 136. The biasing element 162 is of an elastic or shape memory material with a pre-set collapsed state. The elastic structure allows the biasing element 162 to stretch or expand to an expanded state when manipulated and return to the collapsed state when not manipulated. The biasing element 162 is in the expanded state when disposed around the pivotable elements 136. Because, the biasing element 162 is pre-set to the collapsed state, the biasing element 162 applies an inward radial force (compression) to the pivotable elements 136. More particularly, when the system 100 is in the loading configuration and the plurality of pivotable elements 136 are in the first configuration, the biasing element 162 is configured to apply an inward radial force such that the contact surface 150 at each second end 144 of the corresponding pivotable element 136 is held against the delivery catheter and traps the corresponding tether therein. Further, when any pivotable element 136 is in the second configuration, the biasing element 162 exerts an inward radial force on a distal portion of the pivotable element 136 such that when the pivotable element 136 is no longer manipulated by a user to the second configuration, the pivotable element 136 will return to the first configuration. Additionally, when any pivotable element 136 is in the third configuration, the biasing element 162 exerts an inward radial force to bias the pivotable element 136 toward the third configuration. In the embodiment shown, the biasing element is an elastic band made of materials such as, but not limited to, natural rubber or synthetic rubber, polyester, elasthane or any other material suitable for the purposes described herein. However, the biasing element 162 can also be other types of devices that can biased the pivotable elements 136 as described. For example, and not by way of limitation, the biasing element may comprise coils, springs, movable weights, or other similar biasing devices.

Operation and transition of the pivotable elements 136 may now be described in greater detail. In an embodiment described previously with reference to FIGS. 1-2B, each pivotable element 136 of the tool 102 may be disposed in the first configuration, the second configuration, and the third configuration. To transition each pivotable element 136 from the first configuration (FIG. 1) to the second configuration (FIG. 2A), the actuator surface 146 of the respective pivotable element 136 is manipulated by a user with an inward radial force applied thereto in the direction of arrow 137 (FIG. 2A). Application of the inward radial force pivots the pivotable element 136 about the pivot 134, transitioning the pivotable element 136 from the first configuration to the second configuration. If user applied force is removed for the actuating surface 146, the inward radial force (bias) applied to the distal portion of the pivotable element 136 by the biasing element 162 will transition the pivotable element 136 from the second configuration back to the first configuration. To transition each pivotable element 136 from the second configuration (FIG. 2A) to the third configuration (FIG. 2B), the actuator surface 146 of the pivotable element 136 may be manipulated with a longitudinal force applied distally thereto in the direction of arrow 138 (FIG. 2A). Application of the longitudinal force applied distally to the pivotable element 136 slides/translates the pivotable element 136 distally within the corresponding pivotable element slot 124. Further, as the pivotable element 136 slides distally, the pivot slot 152 of the pivotable element 136 slides distally over the pivot 134 such that the pivot 134 effectively slide/translates from the second end 156 to the first end 154 of the pivot slot 152 (FIG. 2B). Due to the shift in location of the pivot 134, the inward radial force applied by the biasing element 162 to the pivotable element 136 retains or locks the pivotable element 136 in the third configuration without continued user manipulation. The pivotable element 136 may be transitioned from the third configuration to the second configuration with application of a longitudinal force applied proximally to the actuator surface 146 in the direction of arrow 140 (FIG. 2B). With application of the longitudinal force in the proximal direction, the pivotable element 136 slides/translates proximally within the corresponding pivotable element slot 124, thus transitioning the pivotable element 136 from the third configuration to the second configuration, and release of the pivotable element 136 transitions it to the first configuration.

Figure 6A:
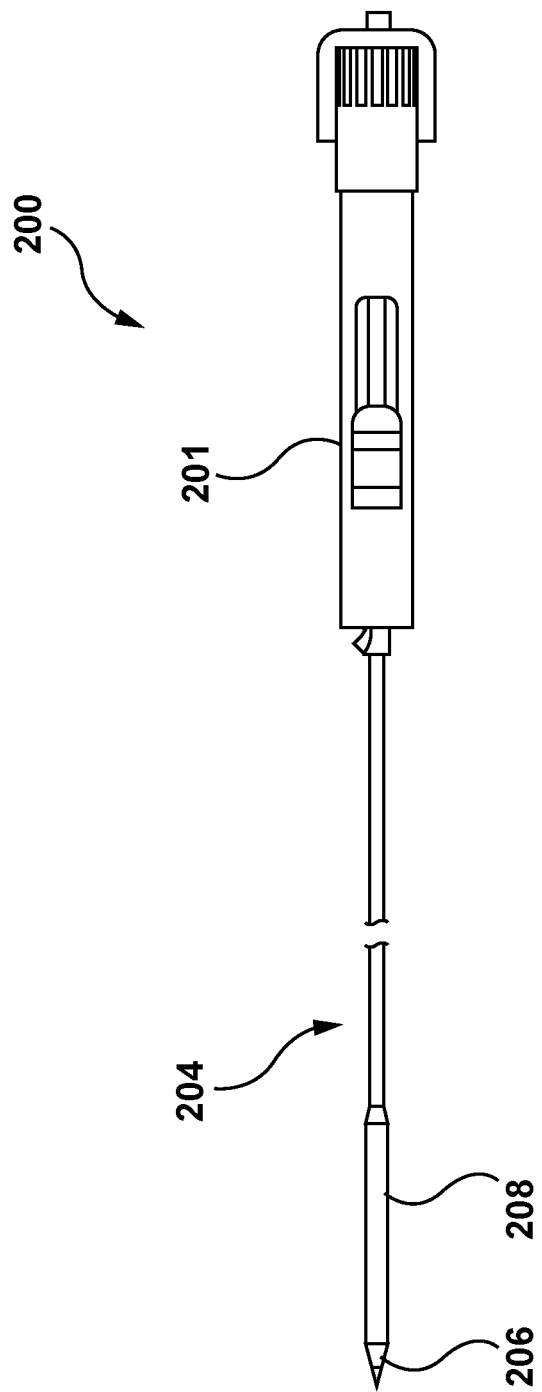
FIG. 6A is a side illustration of a delivery catheter in accordance with an embodiment hereof.
Figure 6B:
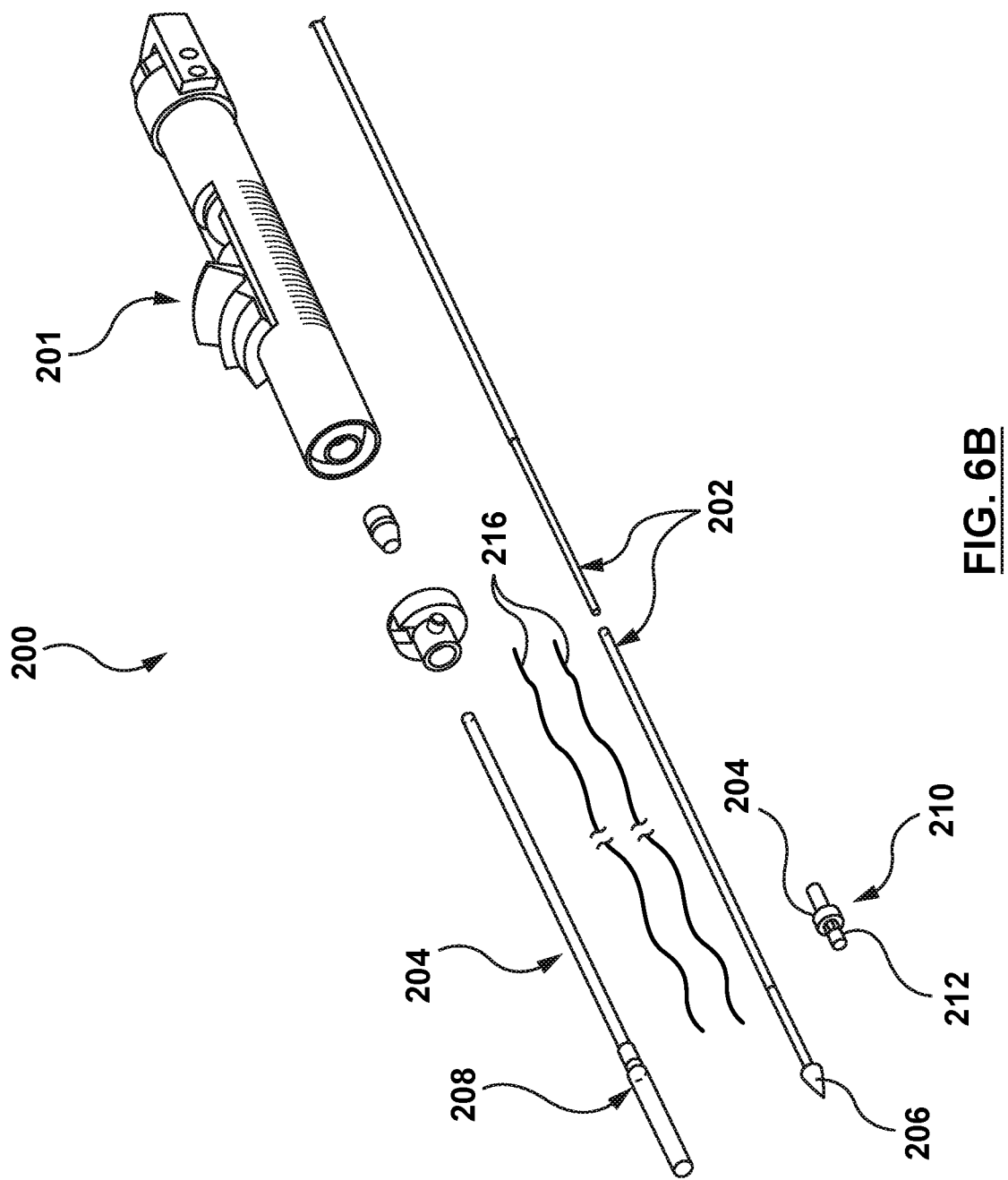
FIG. 6B is an exploded illustration of the delivery catheter of FIG. 6A.

FIGS. 6A-6B show an exemplary embodiment of the delivery catheter 200 of the system 100 with which embodiments of the tool 102 described herein may be used. The delivery catheter 200 is configured to deliver a valve prosthesis to the site of a defective heart valve or defective valve prosthesis. The delivery catheter 200 may be similar to the delivery catheters described in U.S. Patent Application Publication No. 2015/0112430 to Creaven et al., which is incorporated by reference herein in its entirety. In general terms, the delivery catheter 200, also referred to as a delivery device, includes a handle assembly 201, an inner shaft assembly 202, an outer sheath 204 and a distal (dilator) tip 206. The outer sheath 204 and the distal tip 206 combine to form a capsule 208. The capsule 208 is configured to retain a valve prosthesis in a compressed configuration therein for delivery to a desired treatment location. The delivery catheter 200 further includes a valve retainer 210, as shown in FIG. 6B. The valve retainer 210 is configured to retain a portion of the valve prosthesis for loading the valve prosthesis into the capsule 208 of the delivery catheter 200. More specifically, the valve retainer 210 includes at least one tether post 212, a corresponding groove 214 around a proximal portion of each tether post 212, and a corresponding tether 216. Each tether 216 is an elongate member with a first end and a second end coupled to the delivery catheter 200. Each tether is configured to releasably couple the valve prosthesis to the delivery catheter 200 for loading of the valve prosthesis therein, as described in greater detail below. More specifically, each tether 216 is looped through a portion of the valve prosthesis and around the proximal portion of the corresponding tether post 212 (within the corresponding groove 214) such that the valve prosthesis is releasably coupled to the delivery catheter.

Figure 7A:
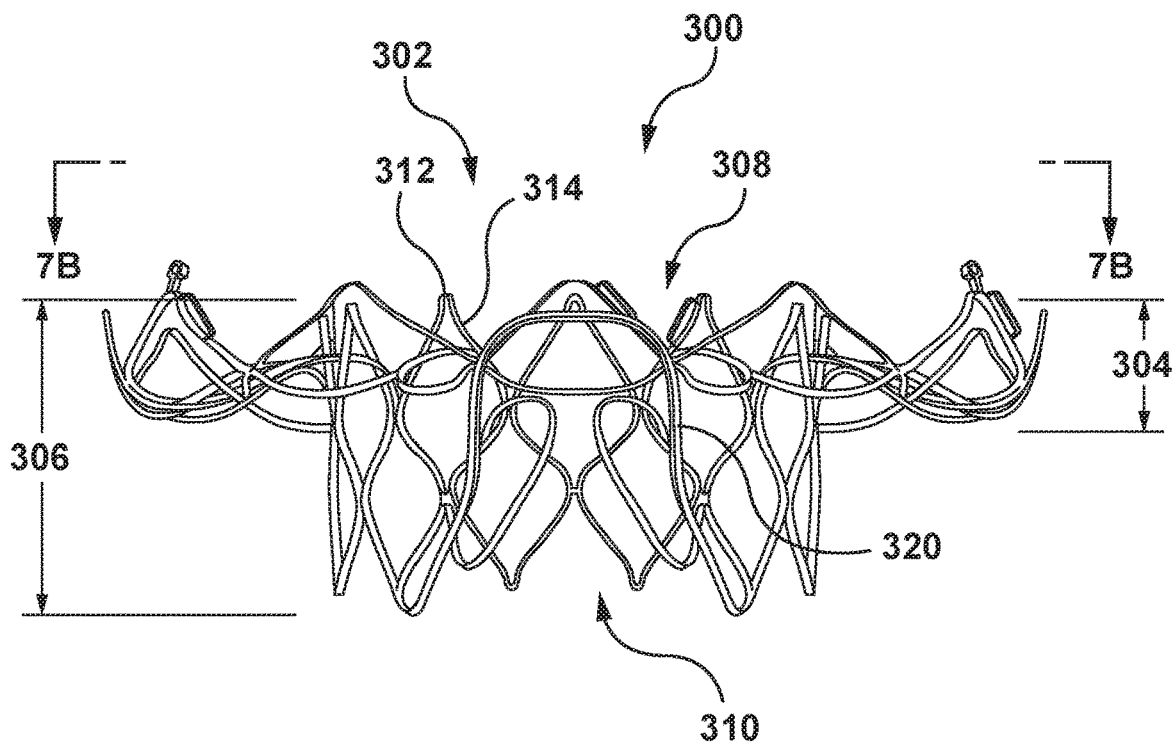
FIG. 7A is a side illustration of a heart valve prosthesis frame with the frame in the normal, or expanded condition.
Figure 7B:
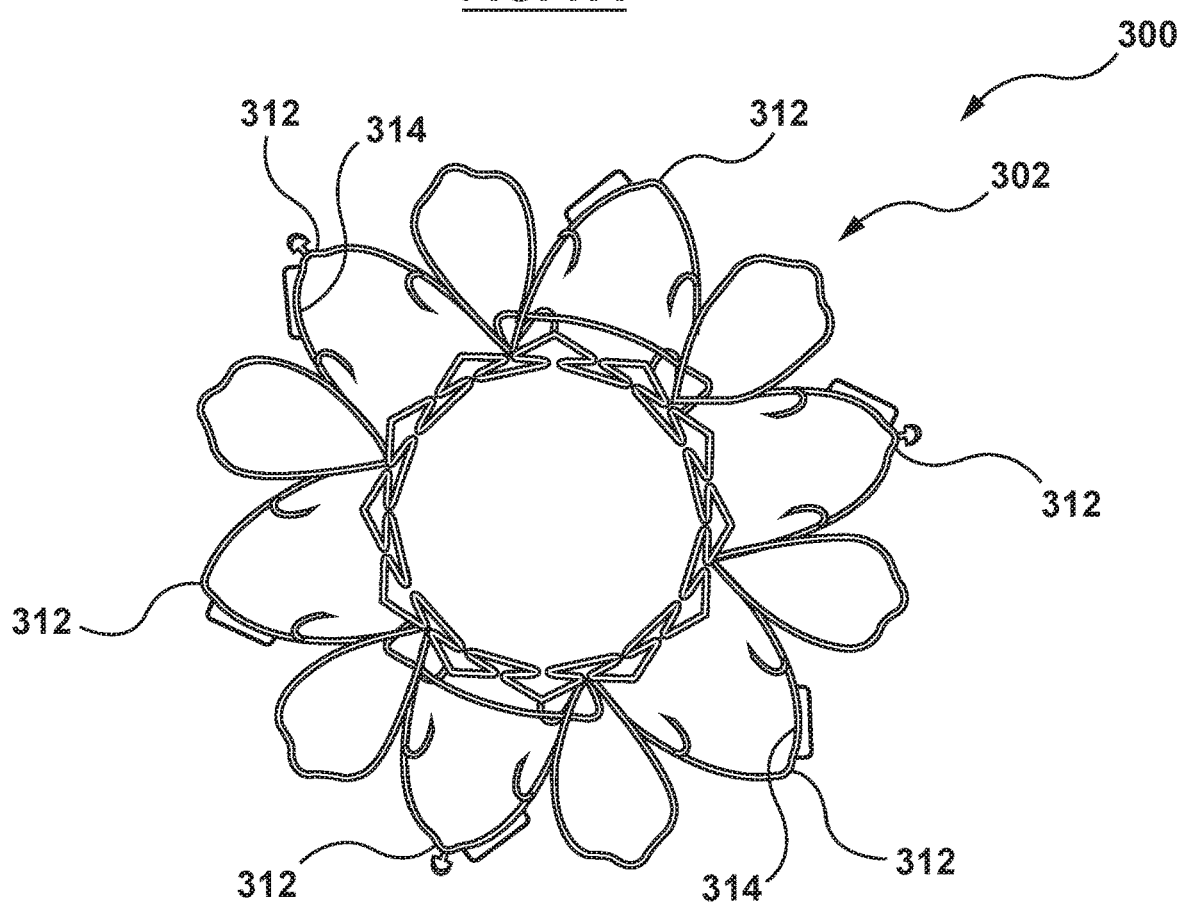
FIG. 7B is an end illustration of the heart valve prosthesis frame of FIG. 7A.

FIGS. 7A-7B illustrate an embodiment of a valve prosthesis 300 for use with the systems, devices and methods described herein. For example, and not by way of limitation, the valve prosthesis 300 may include features described in W.I.P.O. Publication No. WO 2016/133950 to Medtronic Vascular, Inc., the contents of which are incorporated by reference herein in their entirety. More particularly, FIGS. 7A and 7B illustrate a frame 302 in an expanded (deployed) configuration removed from a remainder of the valve prosthesis 300. FIG. 7A is a side view of the frame 302 and FIG. 7B is a top or inflow view of the frame 302 taken in the direction of line 7B-7B in FIG. 7A. The frame 302 may be a unitary structure that defines an inflow portion 304, and a valve-retaining tubular portion 306. A first or inflow end 308 and a second or outflow end 310 of the frame 302 are generally defined by a plurality of respective crowns 312 formed by struts 314 of the frame 302. In embodiments in accordance herewith, the frame 302 may be formed to be self-expanding and therefore can be forced and constrained into the compressed configuration when loaded within a delivery catheter. The frame 302 includes a shape memory to self-expand and return to its natural, expanded configuration, shown in FIG. 7A, upon removal of the constraining force(s) of the delivery catheter.

Although FIGS. 7A-7B show a specific embodiment of an example valve prosthesis 300, it is understood that the devices and methods of the present application may be used with other heart valve prostheses, or other prostheses. Further, as noted above, FIGS. 7A-7B do not show the prosthetic valve which is attached to the frame 302, or other features such as skirts, etc.

Figure 8A:
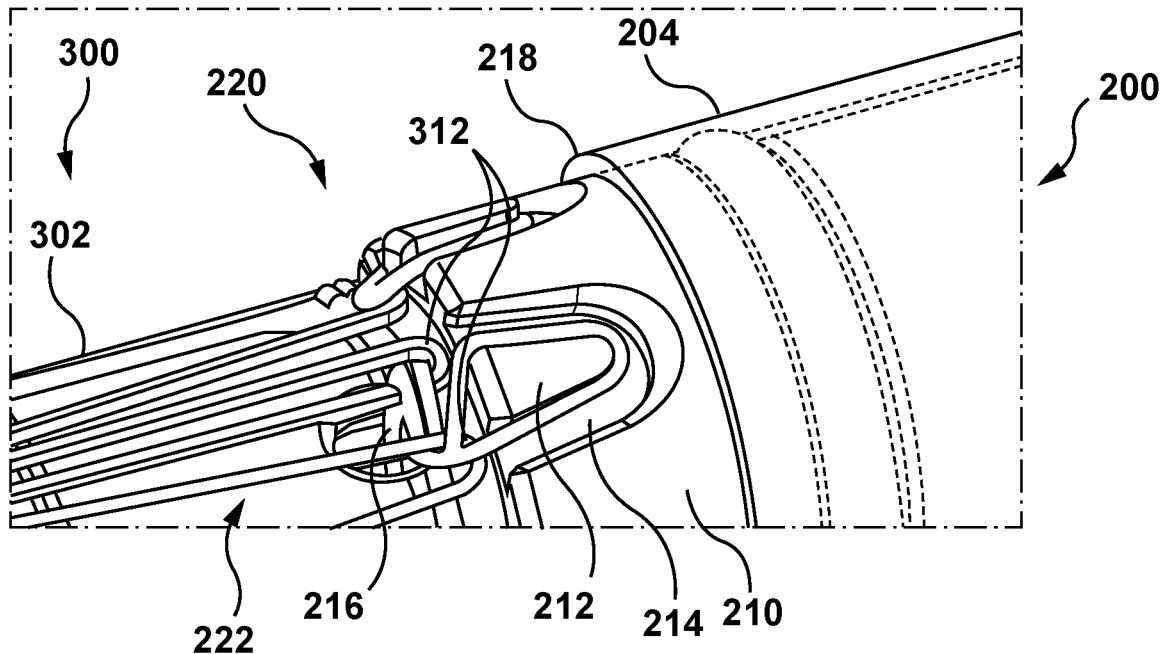
FIG. 8A is a perspective illustration of a portion of the delivery catheter of FIG. 6A in accordance with principles of the present disclosure, along with a portion of the heart valve prosthesis frame of FIG. 7A in a compressed condition.

With the above construction and components in mind and turning to FIG. 8A, the outer sheath 204 of the delivery device 200 serves to retain the tethers 216 relative to the corresponding tether post 212. As a point of reference, FIG. 8A illustrates a distal end 218 of the outer sheath 204 as being proximal the tether posts 212 for ease of illustration. In the delivery state of the delivery catheter 200, however, the distal end 218 is distal the tether posts 212 so as to maintain engagement of the tethers 216 with the tether posts 212. Further, in the delivery state the distal end 218 is located distal of the valve prosthesis 300 to constrain the valve prosthesis 300 to the compressed configuration.

Figure 8B:
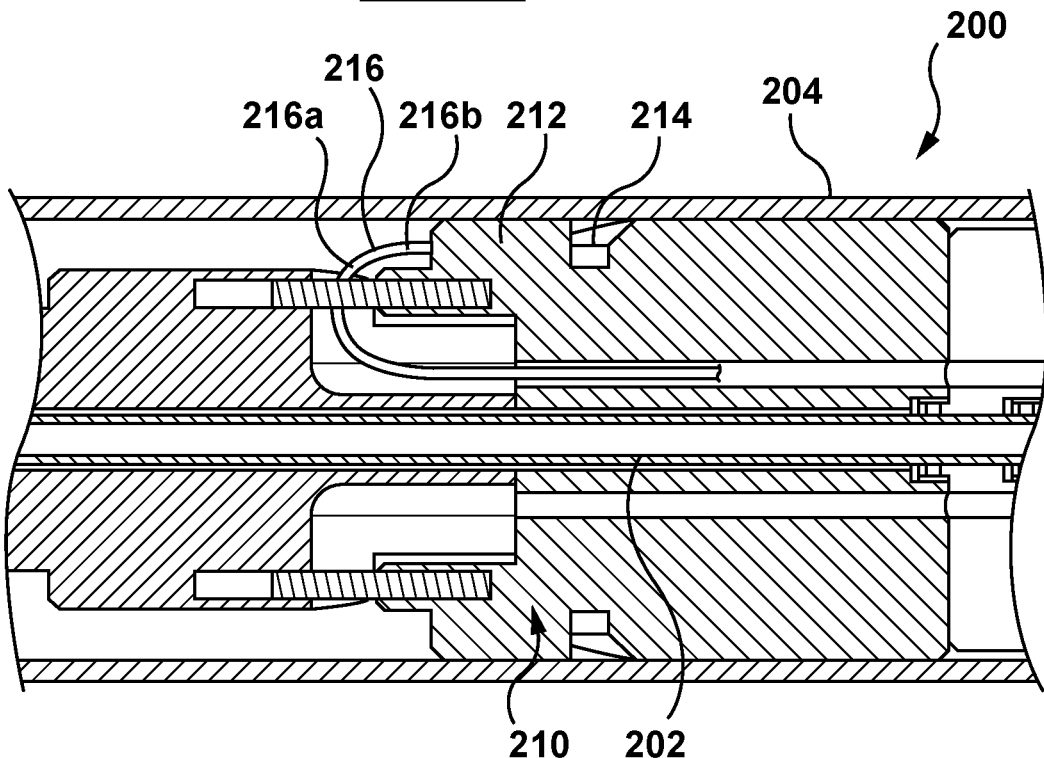
FIG. 8B is a cross-sectional illustration of a portion of the delivery catheter of FIG. 8A.

Connection between the tether(s), the valve prosthesis, and other components of the delivery catheter can assume a variety of forms in accordance with the present disclosure. For example, FIG. 8A illustrates a portion of the delivery catheter 200 coupled to a portion of the frame 302 of the valve prosthesis 300, described previously. The delivery catheter 200 includes the outer sheath 204, the inner shaft assembly 202 (primarily hidden in FIG. 8A but shown in FIG. 8B), and a hub assembly 220. The hub assembly 220 includes a valve support 222, the valve retainer 210, and the plurality of tethers 216. The valve retainer 210 is attached to, or formed by, the inner shaft assembly 202, and forms a plurality of tether posts 212 (one of which is visible in FIG. 8A). A groove 214 is defined about each of the tether posts 212, and is sized to receive a corresponding tether 216 therein and around the tether post 212. In the delivery state generally reflected by FIG. 8A, each of the tethers 216 extends from the valve retainer 210 and is looped through the frame 302 of the valve prosthesis 300. For example, as shown in FIG. 8A, the tether 216 is looped through or around two crowns 312 formed at a first end 304 of the frame 302. FIG. 8B is a simplified cross-sectional view of a portion of the delivery catheter 200, and reflects that the tether 216 is looped about the corresponding tether post 212 within the corresponding groove 214, effectively defining a first and second tether segment 216a, 216b extending from the tether post 212. The tether segments 216a, 216b are looped through the frame 302 (FIG. 8A) and then routed proximally through the valve retainer 210. The tether segments 216a, 216b can extend to the handle assembly 201 (not shown) of the delivery catheter 200 or can be connected to another component of the delivery catheter 200 adapted to facilitate user control over a tension in the tether 216.

With an understanding of the components of the system 100, and with reference to FIGS. 9-14, it is now possible to describe their interaction and a method of loading the valve prosthesis 300 into the delivery catheter 200 utilizing the embodiment of the tool 102 of FIG. 3A.

Figure 9:
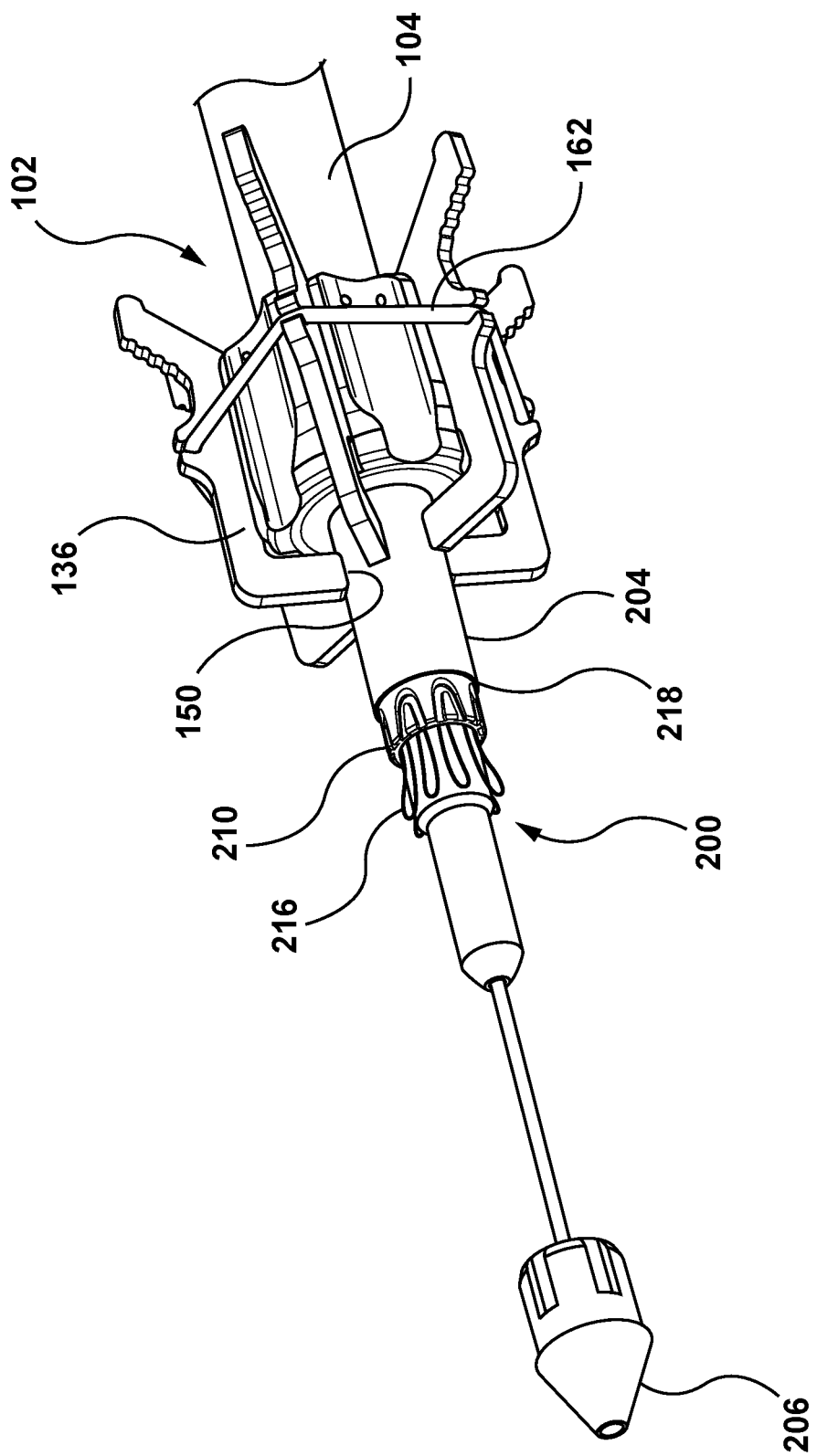
FIG. 9 is a perspective view of the loading tool of FIG. 3A on the delivery catheter of FIG. 6A.

Referring to FIG. 9, the tool 102 is fitted over the distal portion of the delivery catheter 200. More specifically, the distal tip 206 of the delivery catheter 200 is placed into the proximal end 106 of the central passageway 110 of the body portion 104 of the tool 102, and the tool 102 is moved proximally over the distal portion of the delivery catheter 200. Alternatively, the delivery catheter 200 may be advanced distally through the central passageway 410 of the tool 102. The tool 102 is positioned over the distal portion of the outer sheath 204 of the delivery catheter 200. In FIG. 9, the tool 102 is proximal of the distal end 218 of the outer sheath 204. However, the tool 102 is advanced distally until the contact surface 150 of each pivotable element 136 positioned with a distal end of the contact surface 150 aligned with a distal end of the corresponding tether post 212. The tool 102 is aligned circumferentially such that the contact surface 150 of each pivotable element 136 is positioned along the longitudinal centerline of the respective tether post 212. The distal end 218 of the outer sheath 204 is proximal of the valve retainer 210 such that each pivotable element 136 rests on a corresponding tether post 212. In FIG. 9, the tethers 216 are shown in a retracted position. The biasing element places inward radial pressure (compression) on each pivotable element 136 toward the first longitudinal axis LA1 such that the contact surface of each pivotable element 136 remains in physical contact with the respective tether post 212.

Figure 10:
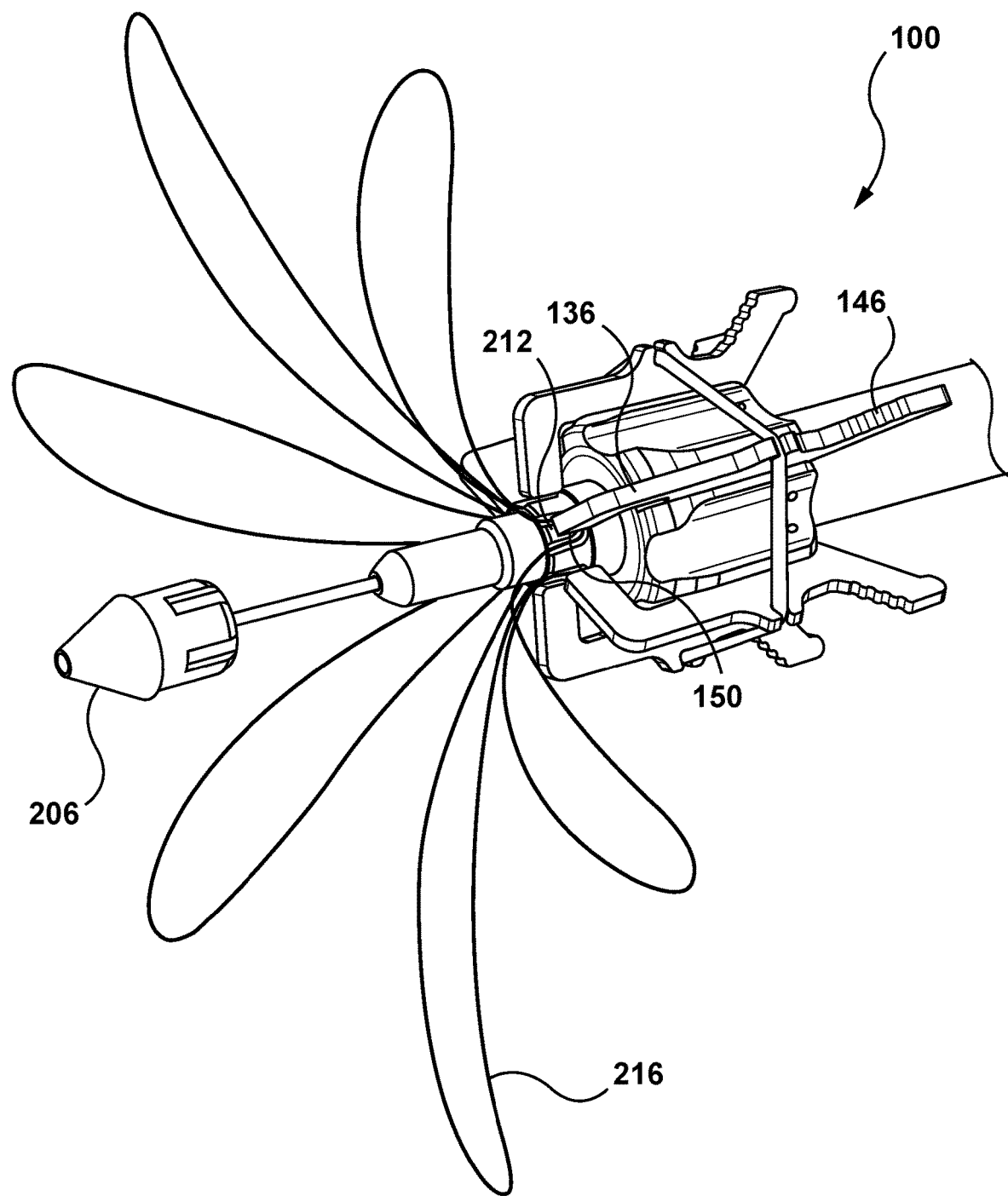
FIG. 10 is a perspective view of the loading tool of FIG. 3A on the delivery catheter of FIG. 6A with a plurality of tethers extended therefrom.

With each contact surface 150 of the plurality of pivotable elements 136 in contact with the respective tether post 212, the plurality of tethers 216 are extended by manipulation of the handle assembly 201 (not shown) to form large loops, as shown in in FIG. 10.

Figure 11:
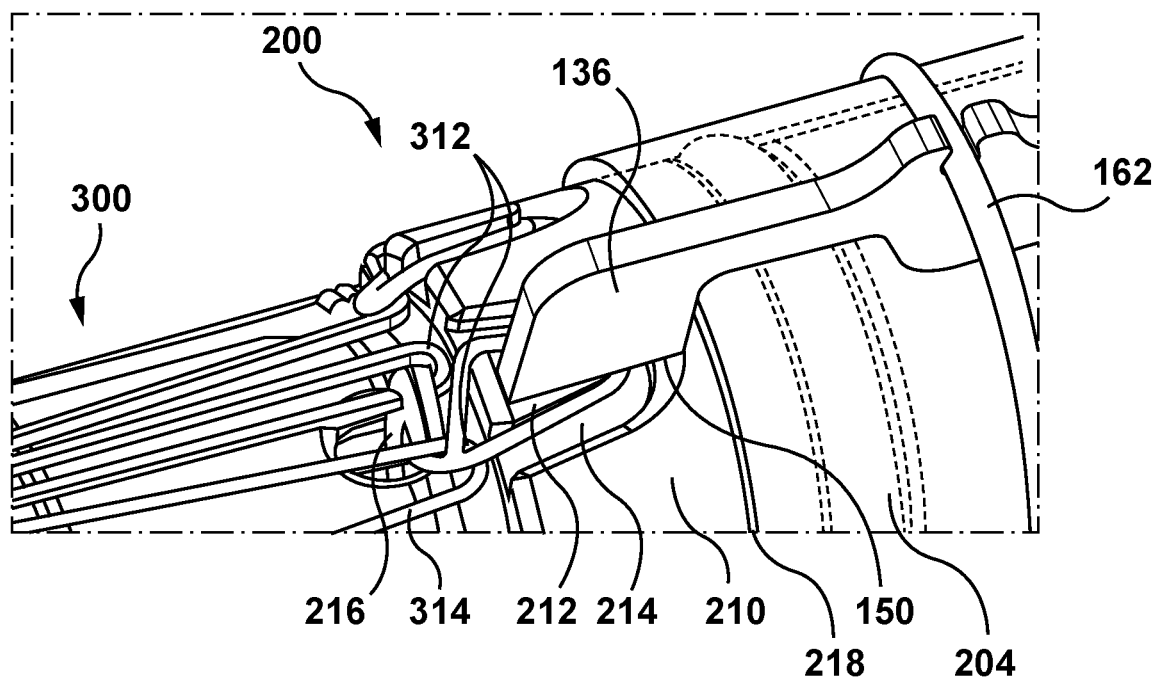
FIG. 11 is a perspective illustration of the delivery catheter of FIG. 6A with the tethers trapped by the loading tool of FIG. 3A.

Once the plurality of tethers 216 are in large loops, the valve prosthesis 300 is connected to the valve retainer 210 of the delivery catheter 200. In an embodiment, each tether 216 is looped through or around two crowns 312 of the valve prosthesis 300, as shown in FIG. 11. Alternately, the tether 216 may be looped around more or fewer crowns 312 or around the struts 314, or any other structure or in any combination suitable for the purposes described herein. Next, the user actuates the corresponding pivotable element 136 to transition the pivotable element 136 from the first configuration to the second configuration. More specifically, an inward radial force is applied to the actuator surface 146 of the respective pivotable element 136 to transition the pivotable element 136 from the first configuration to the second configuration. Once the pivotable element 136 is in the second configuration, the tether 216 is looped around the corresponding tether post 212 within the adjacent groove 214 of the delivery catheter 200, as generally shown in FIG. 11. After the tether 216 is looped around the tether post 212 and within the adjacent groove 214, the user releases the pivotable element 136. More specifically, the user-applied inward radial force on the actuating surface 146 of the pivotable element 136 is released. Upon release of the pivotable element 136, the biasing element 162 exerts an inward radial force on the distal portion of the pivotable element 136 and the pivotable element 136 pivots from the second configuration to the first configuration. Upon transition to the first configuration, the contact surface 150 of the pivotable element 136 contacts the tether post 212 and covers the adjacent groove 214, as shown in FIG. 11. The biasing element 162 exerts an inward radial force on each pivotable elements 136 such that the contact surface 150 of each pivotable element 136 is compressively forced against the respective tether post 212, retaining the corresponding tether 216. This action is completed for each tether 216 and corresponding tether post 212 of the delivery catheter 200. Alternatively, each pivotable element 136 may be transitioned from the second to the third configuration before looping each tether 216 around the corresponding tether post 212 and within the adjacent groove 214, and then returned to the first configuration after each tether 216 is disposed in the respective groove 214.

When the plurality of tethers 216 are retained by the valve retainer 210 and the plurality of pivotable elements 136 disposed thereon, the handle assembly 201 (not shown) is manipulated by the user and the plurality of tethers 216 are retracted to remove slack. Once the slack is removed, the outer sheath 204 of the delivery catheter 200 is moved distally by manipulating the handle assembly 201 (not shown). As the outer sheath 204 advances distally, it will lift (slide under) each contact surface 150 of each pivotable element 136, thereby covering the respective grooves 214 and tether posts 212 and retaining the tether(s) 216 therein. Each tether 216 is thus retained in the corresponding groove 214 and around the corresponding tether post 212 by an inner surface of the outer sheath 204, as shown in FIG. 12, with the plurality of pivotable elements 136 in the third configuration for clarity (i.e., the pivotable elements 136 would be in the first configuration). Thus, the valve prosthesis 300 is releasably coupled to the delivery catheter 200.

Figure 13A:
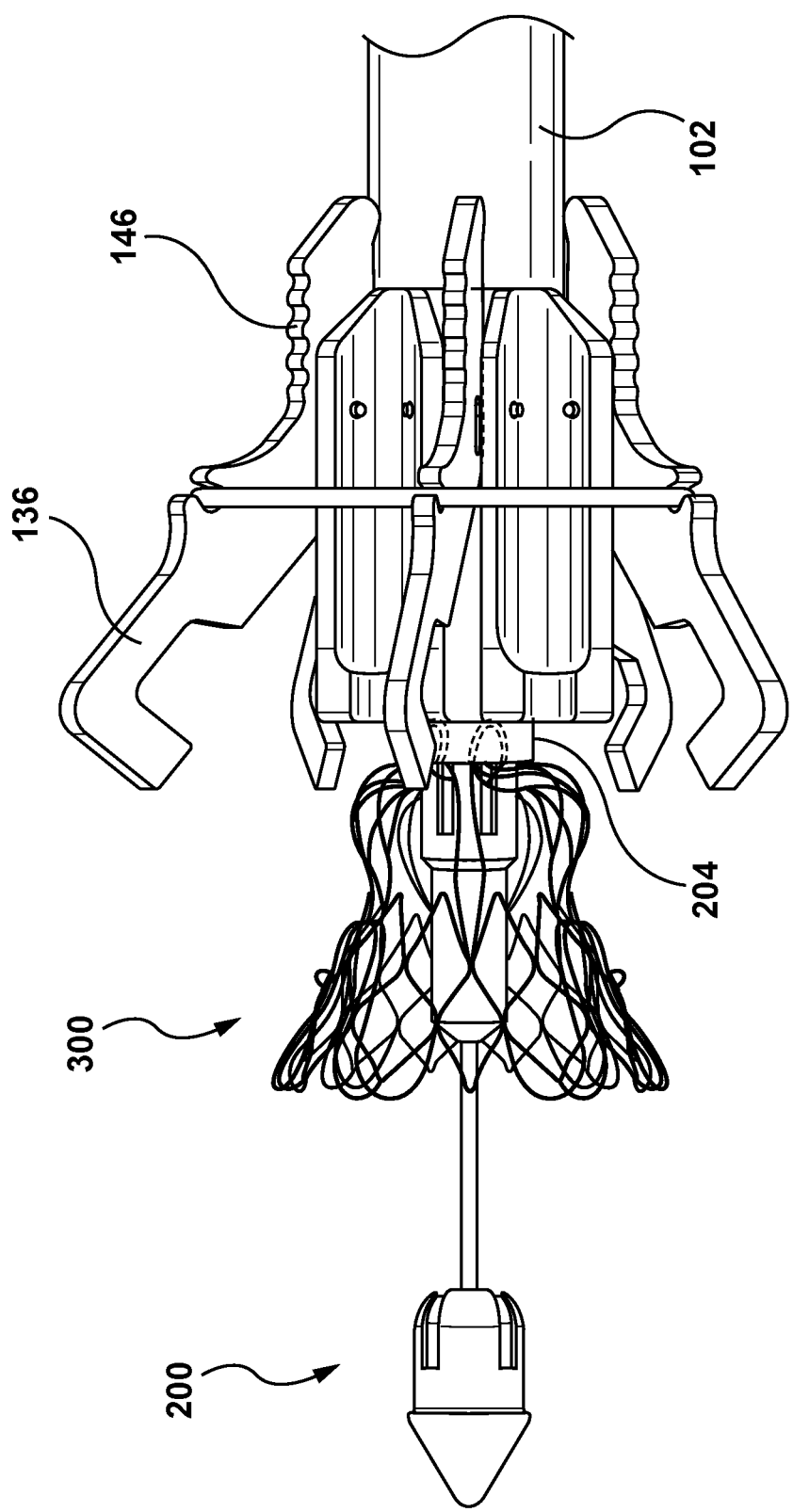
FIGS. 13A-13D are perspective illustrations of the loading of the valve prosthesis of FIG. 7A into a capsule of the delivery catheter of FIG. 6A with the tool of FIG. 3A.

Once the valve prosthesis 300 is releasably coupled to the delivery catheter 200, each pivotable element 136 is actuated such that each pivotable element 136 transitions from the first configuration to the second, as previously described, and then to the third configuration, as generally reflected in FIG. 13A. More specifically, the actuator surface 146 is manipulated with application of a longitudinal force applied distally thereto. The longitudinal force applied distally to the actuator surface 146 of the pivotable element 136 slides/translates the pivotable element 136 distally within the corresponding pivotable element slot 124, transitioning the pivotable element 136 from the second configuration to the third configuration. As described previously, the pivotable element 136 will remain in the third configuration until transitioned by the user to the second configuration. This action is completed for each pivotable element 136 of the tool 102.

Figure 13B:
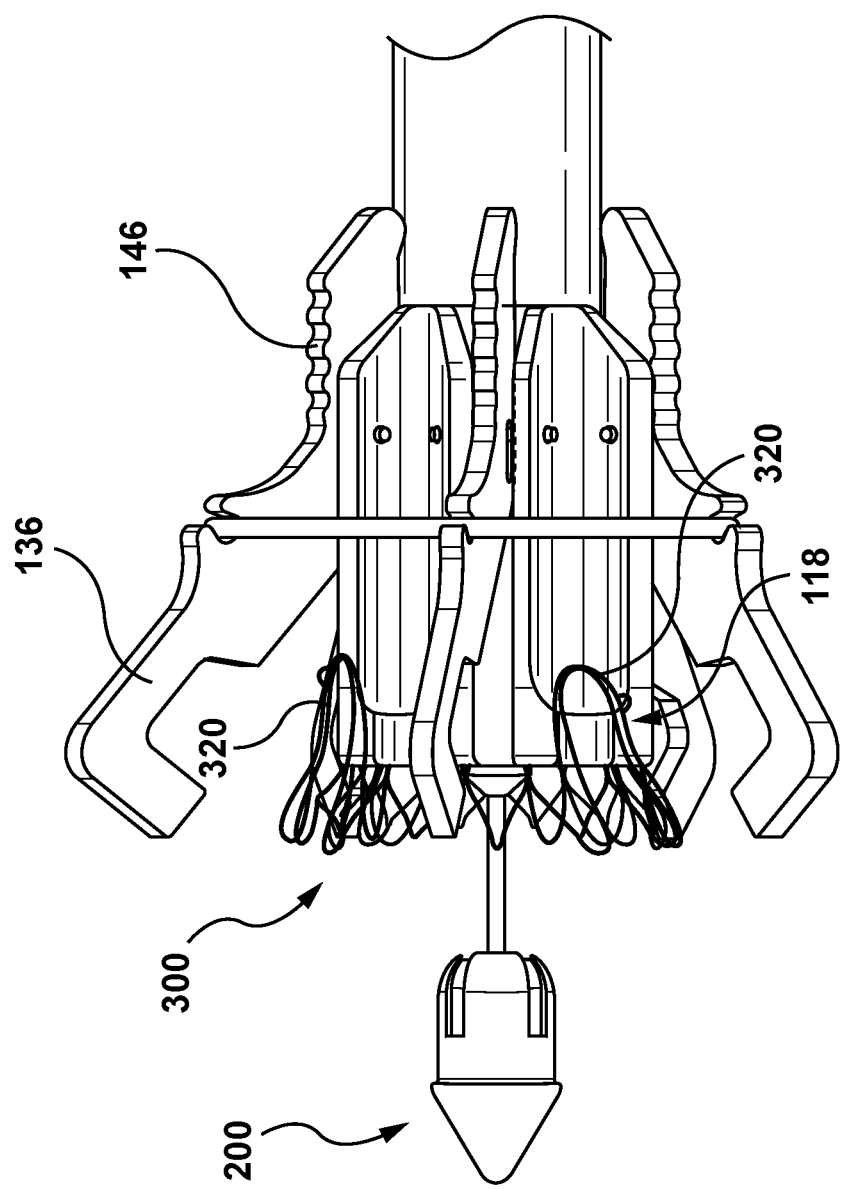
Figure 13C:
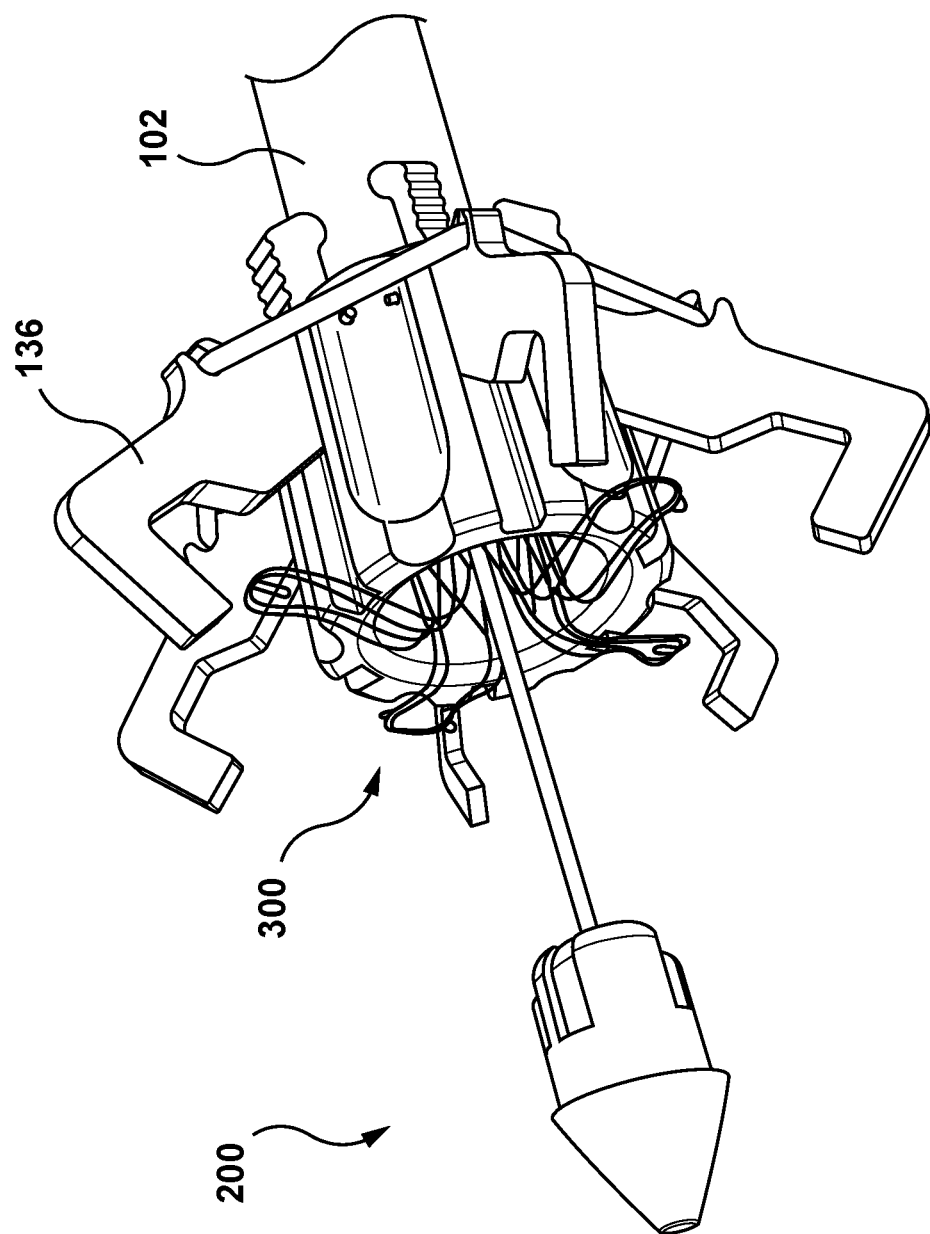
Figure 13D:
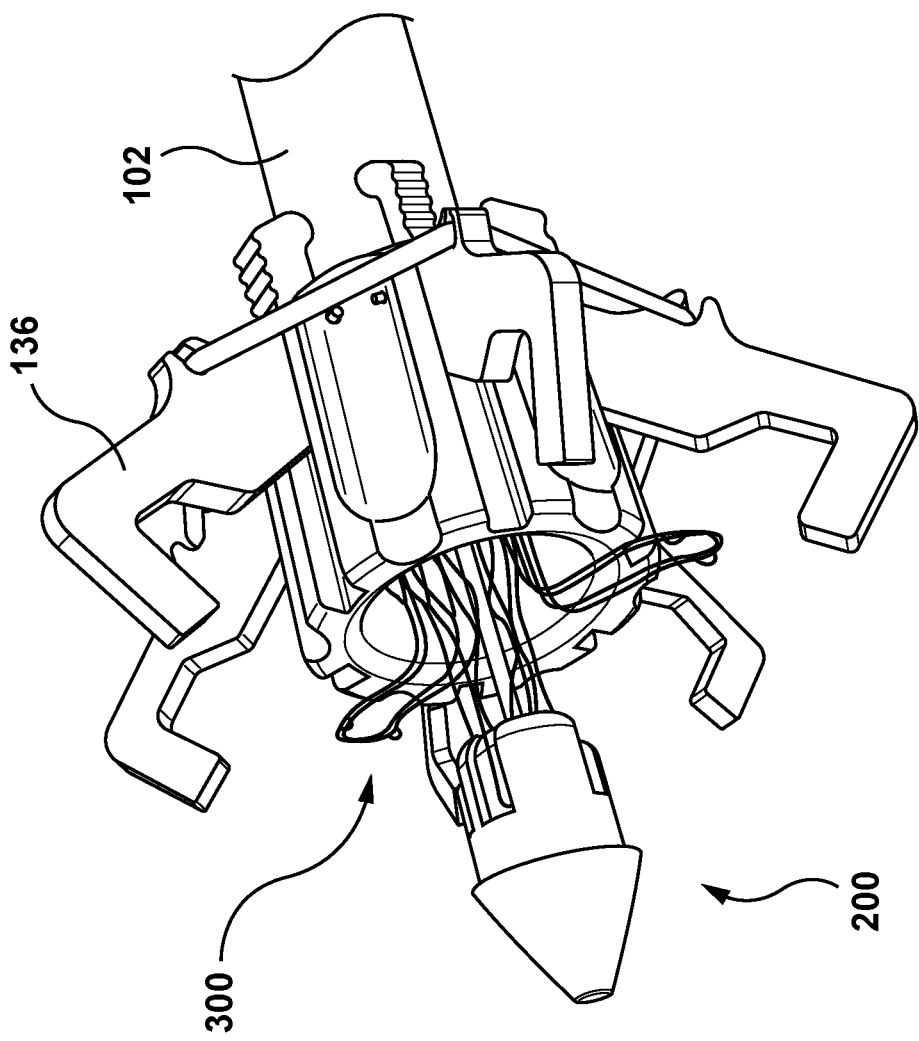
Figure 14:
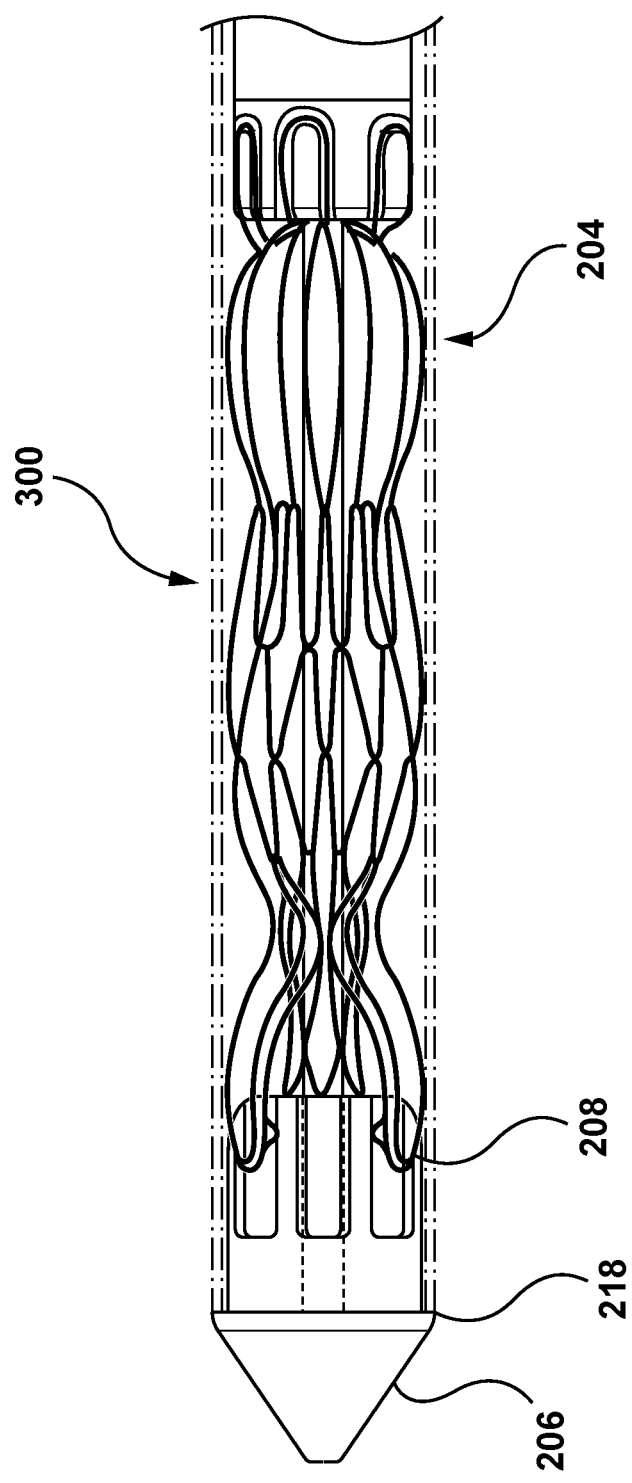
FIG. 14 is a perspective illustration of the loaded capsule of the delivery catheter of FIG. 6A.

With the valve prosthesis 300 releasably coupled to the delivery catheter 200 and each pivotable element 136 in the third configuration, the tool is advanced distally relative to the outer sheath 204 such that the distal end 118 of the tool 102 is distal of the distal end 218 of the outer sheath 204. Next, the outer sheath 204 is advanced distally by manipulation of the handle assembly 201 (not shown) and the tool 102 is advanced distally with the outer sheath 204 such that the valve prosthesis 300 is radially collapsed within the advancing outer sheath 204 (FIG. 13A) and the tool 102. The tapered portion 118 (FIG. 13B) of the tool 102 assists in radially collapsing the valve prosthesis 300. If the valve prosthesis includes arms 320, as shown, the arms 320 may be placed over the tool (FIG. 13B) such that the arms 320 evert as the outer sheath 204 and the tool 102 are advanced, as shown in FIG. 13B-13D. FIGS. 13A-13D illustrate the slow radial collapse and loading of the valve prosthesis 300 into the outer sheath 204 of the delivery catheter 200. The outer sheath 204 is advanced until the distal end 218 contacts a proximal end of the distal tip 206, as shown in FIG. 14. The compressed valve prosthesis 300 is now retained within the capsule 208 of the delivery catheter 200. The loading tool 102 may now be removed from the delivery catheter 200 by sliding it distally off the distal end of the delivery catheter 200.

While the preceding method is described with specific configurations of the plurality of pivotable elements 136 in a particular step, this is not meant to limit the method, and the order of the particular steps and configuration of each pivotable element 136 in each step may be altered by the user as desired or for specific applications or based upon user preference. For example, any time a pivotable element is transitioned to the second configuration, the user may optionally transition the pivotable element 136 to the third configuration. Similarly, any time a pivotable element is transitioned to the third configuration, the user may opt to leave the pivotable element in the second configuration.

While the previous procedure is described with reference to the embodiment of FIG. 3A, other embodiments of the tool 102, such as, but not limited to the embodiment of FIG. 3B, may be utilized with the similar procedure with minor modifications. For example, in the embodiment of the tool 102' of FIG. 3B, the procedure is modified with the additional step of positioning a collapsing cone at the distal end of the tool 102' after the valve prosthesis 300 is releasably coupled to the delivery catheter 200 and prior to collapsing the valve prosthesis 300 into the capsule 208. As would be understood by one skilled in the art, the collapsing cone is positioned to assist is collapsing the valve prosthesis 300 into a radially compressed configuration for loading into the capsule 208 of the delivery catheter 200.

FIGS. 15-25 illustrate a system 400 and a method for loading a valve prosthesis into a delivery catheter in accordance with another embodiment hereof. The system 400 includes a loading tool 402 (hereafter referred to as "tool 402" for sake of simplicity) and a delivery catheter, such as the delivery catheter 200 described previously. The system 400 further includes a loading configuration wherein the delivery catheter 200 is received within a central passageway 410 of the tool 402 for loading of a valve prosthesis (not shown) therein, and a delivery configuration wherein the delivery catheter 200 is not received within the tool 402. The system 400 is configured such that when the system 400 is in the loading configuration, the loading tool 402 assists in loading the valve prosthesis into the delivery catheter 200, as described in greater detail below.

In an embodiment, as shown in FIGS. 15-19, the tool 402 is similar to the tool 102 described previously. In general, the tool 402 includes a body portion 404, the central passageway 410, a plurality of pivotable arms 436, and a biasing element 462. The loading tool 402 is configured to assist in the loading of a valve prosthesis, such as the valve prosthesis 300 described previously, into a capsule of the delivery catheter, such as the capsule 208 of the delivery catheter 200 described previously. Therefore, similar construction and alternatives of the tool 402 will not be described here.

However, unlike the tool 102, the tool 402 includes a securing device 470. Further, in an embodiment, the tool 402 includes a pivot bore 432 instead of a pivot slot.

Figure 15:
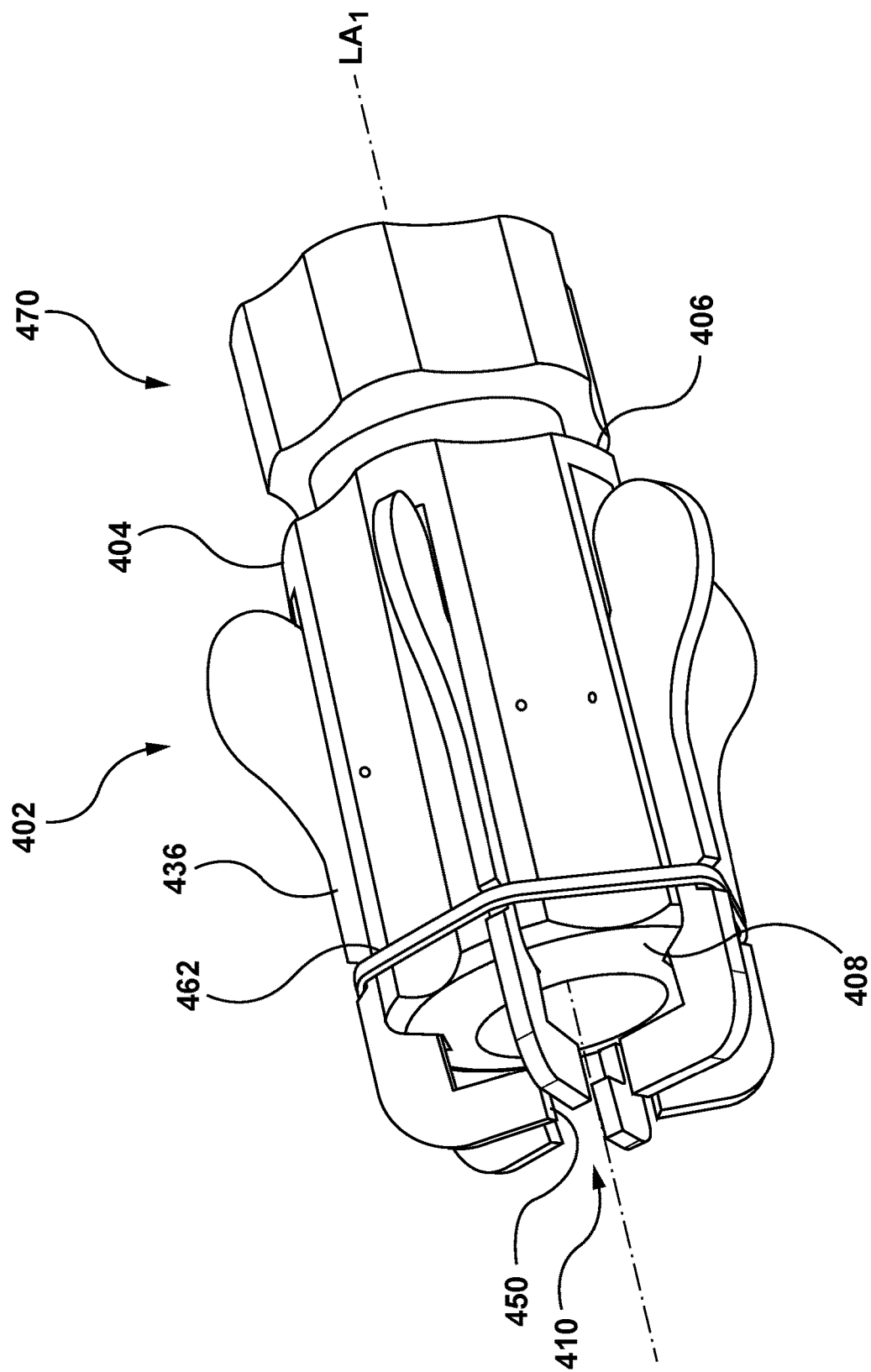
FIG. 15 is a perspective illustration of a loading tool in accordance with another embodiment hereof, in a first configuration.
Figure 17:
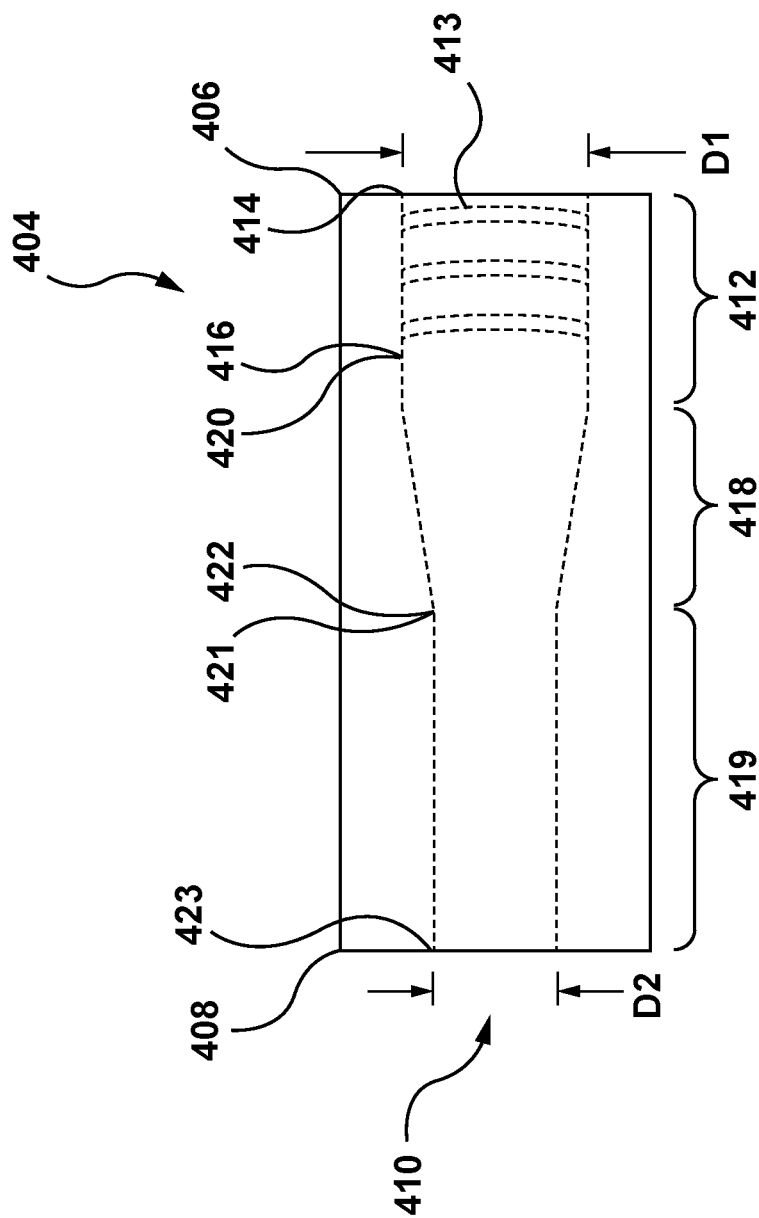
FIG. 17 is a side illustration of a body portion of the loading tool of FIG. 15 according to another embodiment hereof.

The body portion 404 of the tool 402 includes a proximal end 406, a distal end 408 and the central passageway 410, as shown in FIG. 15 and in greater detail in FIG. 17. The central passageway 410 extends distally from the proximal end 406 to the distal end 408. The central passageway 410 is an opening (bore or lumen) extending through the entirety of the longitudinal center of the body portion 404 along a first longitudinal axis LA1. The body portion 404 is configured to slide onto (over), or alternatively, receive within the central passageway 410 the distal portion of the delivery catheter. When positioned over the distal portion of the delivery catheter, the body portion 404 is further configured to assist in loading the valve prosthesis into the delivery catheter. In an embodiment, the central passageway 410 is further configured to receive a portion of the securing device 470 in a proximal portion thereof.

In the embodiment shown in FIG. 17, the central passageway 410 (shown as the dotted line) of the body portion 404 includes a threadable portion 412, a tapered portion 418, and a distal portion 419. The threadable portion 412 extends distally from a proximal end 414 co-located with the proximal end 406 of the body portion 404 to a distal end 416, proximal of the distal end 408 of the body portion 404. The proximal portion 412 is of a generally cylindrical shape and of a consistent first diameter D1. In an embodiment, the inner surface of the proximal portion 412 includes a plurality of helical threads 413 (hereafter referred to as "threads 413" for sake of simplicity). The threads 413 are configured to receive and engage a corresponding plurality of helical threads 498 (hereafter referred to as "threads 498" for sake of simplicity) of the securing device 470 when disposed therein, as described in greater detail below. The tapered portion 418 of the central passageway 410 extends from a proximal end 420 coupled to the distal end 416 of the proximal portion 412 distally to a distal end 422, located proximal of the distal end 414. The tapered portion 418 tapers radially inward from the proximal end 420 with the first diameter D1 to the distal end 422 with a second diameter D2, wherein the second diameter D2 is smaller than the first diameter D1. Thus, the tapered portion 418 is of a generally frustoconical in shape with the larger, first diameter D1 at the proximal end 420 tapering down (reducing in diameter) distally to the distal end 422. The tapered portion 418 is configured to provide increasing inward radial force on a distal portion of the securing device 470 when the securing device 470 is disposed therein, as described in greater detail below. The distal portion 419 extends distally from a proximal end 421 co-located with the distal end 422 of the tapered portion 418 to a distal end 423, co-located at the distal end 408 of the body portion 404. The proximal portion 412 is of a generally cylindrical shape and of a consistent second diameter D2. While the proximal portion 412 is shown with a specific number, pitch, and handedness of threads 413, this is not meant to limit the invention, and the threads 413 may be of a greater or fewer number, with a greater or lesser pitch and a different handedness. Moreover, the threads 413 may be an integral component of the proximal portion 412 of the central passageway 410 or may be a separate component coupled to proximal portion 412 of the central passageway 410 by methods such as, but not limited to adhesives, bonding, or other methods suitable for the purposes described herein. The body portion 404 may be formed of metal and/or polymeric materials such as, but not limited to polyethylene, PEBA, polyamide and/or combinations thereof. The body portion 404 may be formed by various methods, non-limiting examples of which include machining, extrusion, molding, or other methods and combinations of methods.

Figure 16:
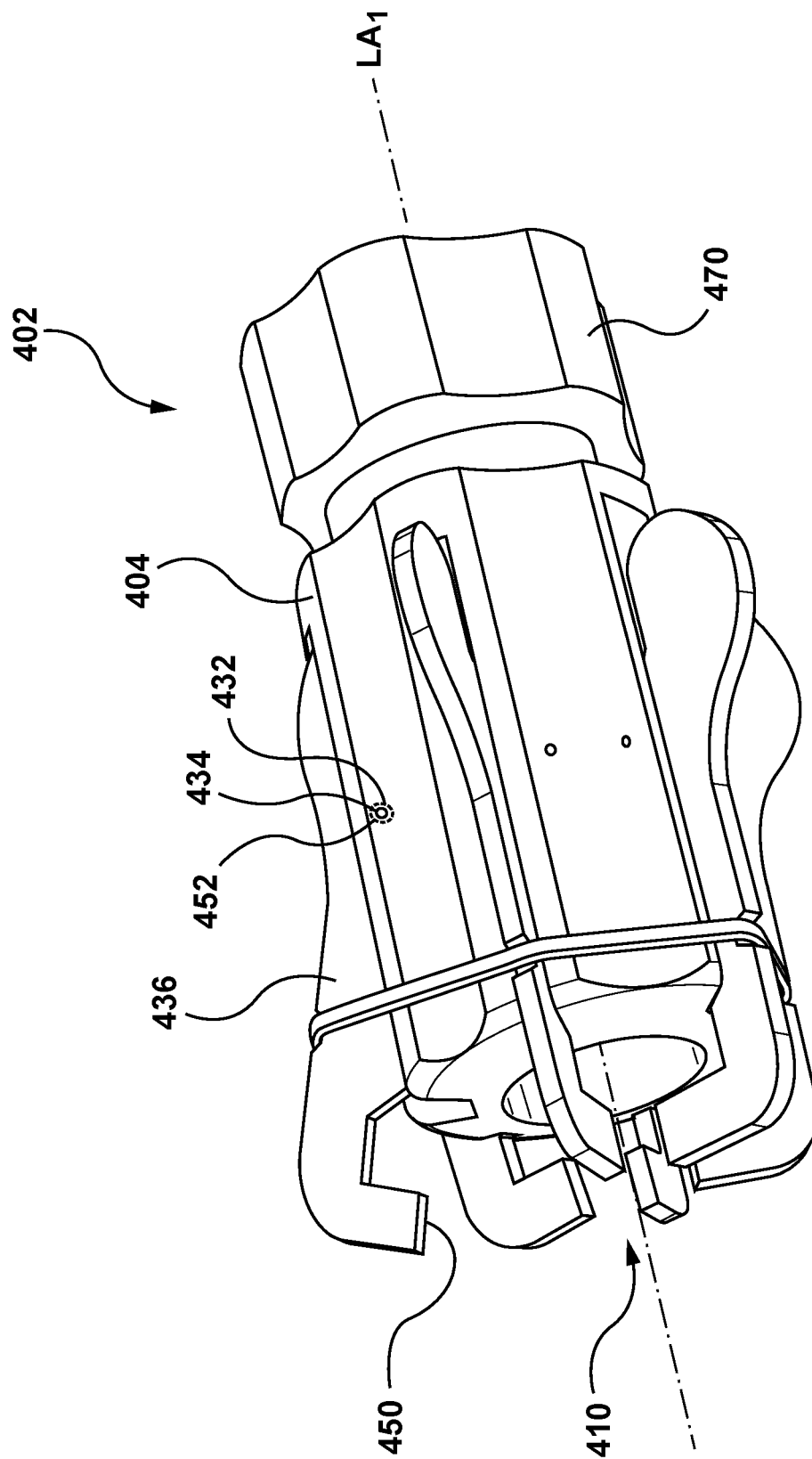
FIG. 16 is a perspective illustration of the loading tool of FIG. 15 in a second configuration.

The tool 402 includes the plurality of pivotable elements 436. In an embodiment shown in FIG. 15 and in greater detail in FIG. 18, each pivotable element 436 is similar in construction and alternatives to the plurality of pivotable elements 136 of FIG. 1, except that each pivotable element 436 includes a pivot bore 452 rather than a pivot slot. Each pivot bore 452 is a circular aperture extending transversely through the pivotable element 436 and aligned with the corresponding pivot bore 432 such that a corresponding pivot 434 may be disposed therethrough, as shown in FIG. 16. Thus, the pivotable element 436 may pivot about the corresponding pivot 434. Each pivotable element 436 is pivotable between a first (closed) configuration and a second (open) configuration. In the first configuration, a contact surface 450 of the pivotable element 436 contacts an outer surface of the delivery catheter 200 when the system 400 is in the loading configuration, as shown in FIG. 15. In the second configuration, the contact surface 450 of the respective pivotable element 436 is disposed radially outward of the first longitudinal axis LA1, as shown in FIG. 16, and does not contact an outer surface of the delivery catheter 200 when the system 400 is in the loading configuration.

Figure 18:
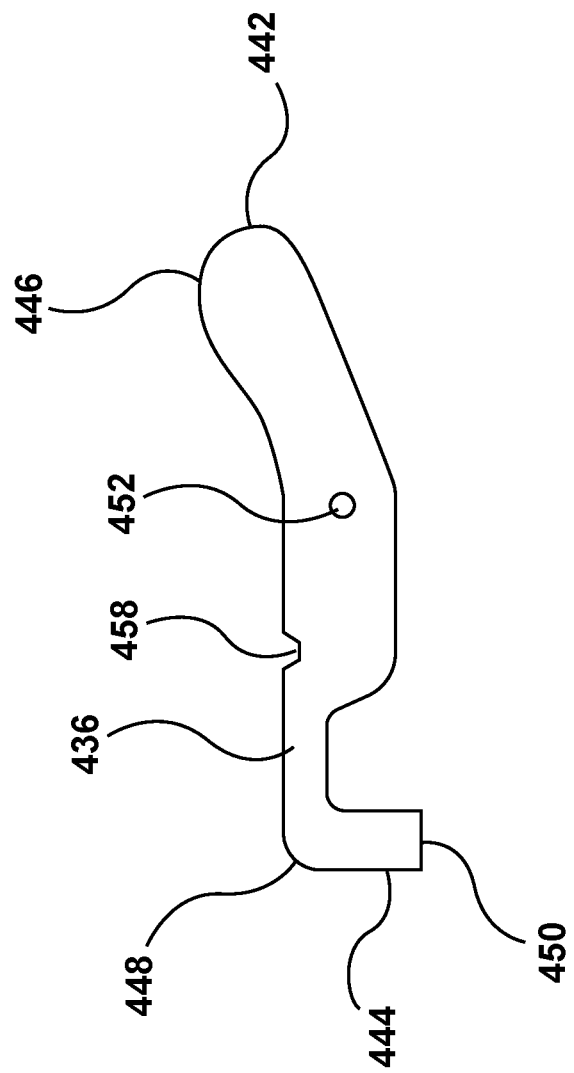
FIG. 18 is a side illustration of a pivotable element of the loading tool of FIG. 15 in accordance with an embodiment hereof.

The biasing element 462 is similar to the biasing element 162 described previously. Therefore, details of the biasing element 462 will not be included here. In an embodiment, the biasing element 462 is an elastic band disposed circumferentially around the pivotable elements 436. The biasing element 462 is disposed in a slot 458 in each of the pivotable elements 436 (FIG. 18).

The tool 402 further includes the securing device 470. The securing device 470 is configured to secure or releasably couple the tool 402 to the delivery catheter during loading of the valve prosthesis into the delivery catheter. In an embodiment, shown in FIG. 19, the securing device 470 is configured to be threadably engaged with the central passageway 410 (FIG. 15) and tightenable onto the delivery catheter. More specifically, a distal portion of the securing device 470 is configured to be received within a corresponding portion of the central passageway 410 (FIG. 15). In an embodiment, the securing device 470 includes a body 472 and a lumen 474. The body 472 of the securing device 470 includes a proximal end 476, a distal end 478 and the lumen 474. The lumen 474 extends from the proximal end 476 to the distal end 478. The lumen 474 is an opening (bore) extending through the entirety of the longitudinal center of the body 472 of the securing device 470 along a longitudinal axis LA2. The lumen 474 includes a diameter D3 and is configured to receive a distal portion of the delivery catheter therethrough. In the embodiment shown in FIG. 19, the body 472 includes a gripable portion 480, a threaded portion 486, and a collet portion or plurality of fingers 492. The body 472, including the gripable portion 480, the threaded portion 486, and the plurality of fingers 492 of the securing device 470 may be formed of metal and/or polymeric materials such as, but not limited to polyethylene, PEBA, polyamide and/or combinations thereof. The body 472 and its components may be formed by various methods, non-limiting examples of which include machining, extrusion, molding, or other methods and combinations of methods.

The gripable portion 480 extends distally from a proximal end 482 co-located with the proximal end 476 of the body 472 to a distal end 484, proximal of the distal end 478 of the body 472. The gripable portion 480 is of a generally cylindrical shape and is configured to be disposed proximal of the body portion 404 of the tool 402. The gripable portion 480 is further configured such that manipulation of the gripable portion 480 releasably couples or uncouples the securing device 470 to the body portion 404, and hence releasably couples or uncouples the tool 402 to the delivery device 200 disposed therethrough. The outer radial surface of the gripable portion 480 may include a shape or texture thereon to assist in manipulation of the gripable portion 480.

Figure 19:
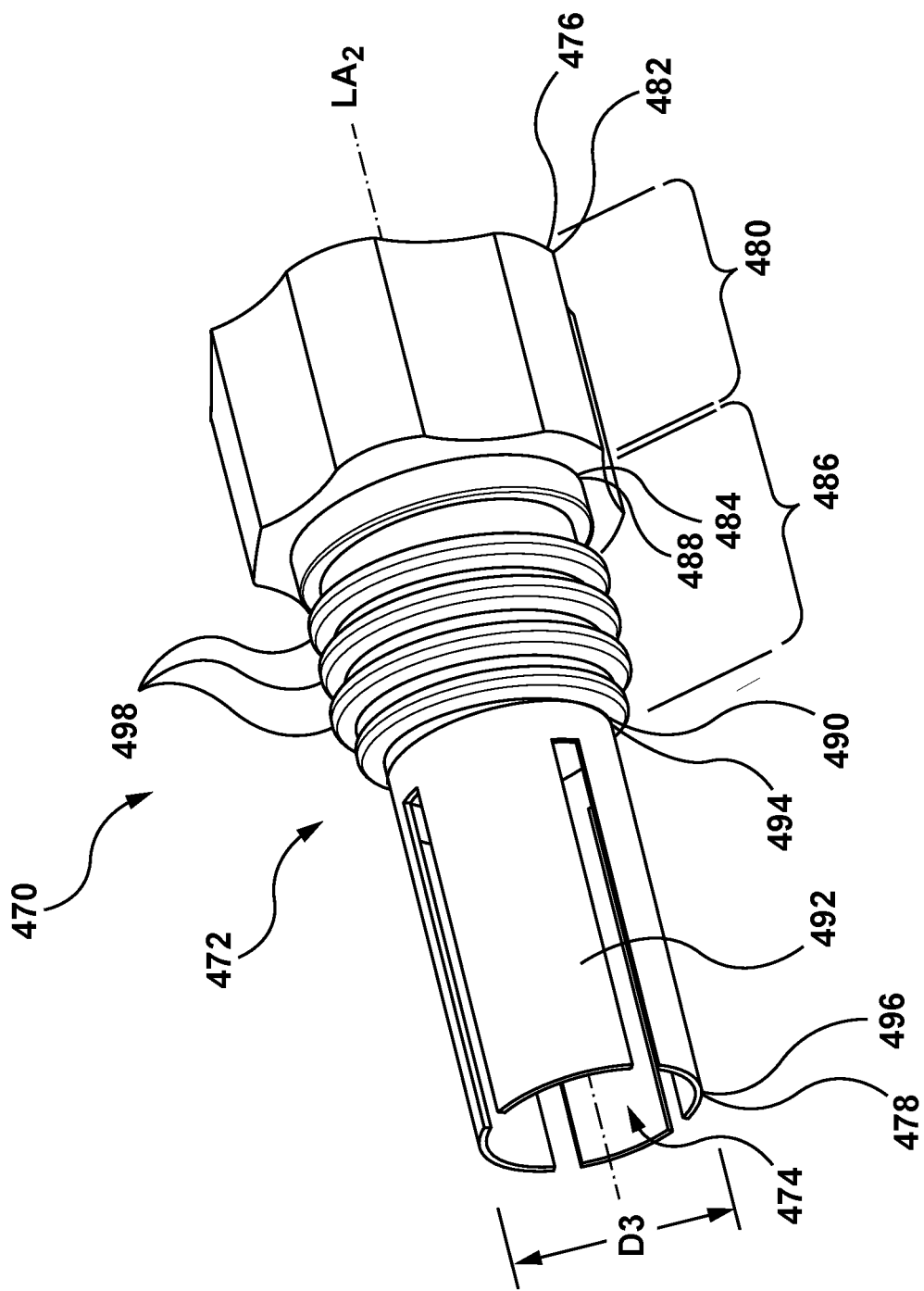
FIG. 19 is a perspective illustration of a securing device of the loading tool of FIG. 15 in accordance with an embodiment hereof.

The threaded portion 486 of the securing device 470 extends from a proximal end 488 coupled to the distal end 484 of the gripable portion 480 distally to a distal end 490, located proximal of the distal end 478 of the securing device 470. The threaded portion 486 is of a generally cylindrical shape and is configured to be disposed within the proximal portion 412 of the body portion 404 of the tool 402. In an embodiment, the outer surface of the threaded portion 486 includes the threads 498. The threads 498 are configured to engage the corresponding threads 413 of the body portion 404 of the tool 402 such that rotation of the securing device 470 and the threads 498 coupled thereto translates (axially moves) the securing device 470 distally or proximally within the central passageway 410 of the body portion 404. The threaded portion 486 is shown in FIG. 19 with a specific number, pitch, and handedness of threads 498, however, this is not meant to limit the invention and the threads 498 may be of a greater or fewer number, with a greater or smaller pitch and a different handedness corresponding to the threads 413 of the central passageway 410. The threads 498 may be an integral component of the securing device 470 or may be a separate component coupled to the securing device by methods such as, but not limited to adhesives, bonding, or other methods suitable for the purposes described herein.

The plurality of fingers 492 extend distally from a proximal end 494 co-located with the distal end 490 of the threaded portion 486 to a distal end 496. The plurality of fingers 492 are configured to be disposed within the tapered portion 418 (FIG. 17) of the central passageway 410 body portion 404 of the tool 402. The plurality of fingers 492 are further configured to deform radially upon application of a radial force applied thereto. While the securing device 470 is shown with four (4) fingers 492, this is not meant to limit the invention, and more or fewer fingers 492 may be utilized.

With an understanding of the components of the system 400, and with reference to FIGS. 20-26, it is now possible to describe a method of loading the valve prosthesis using the exemplary valve prosthesis 300, described previously with respect to FIGS. 7A-7B into the delivery catheter 200, described previously with respect to FIGS. 6A-6B and FIGS. 8A-8B utilizing the embodiment of the tool 402 of FIG. 15.

Figure 20:
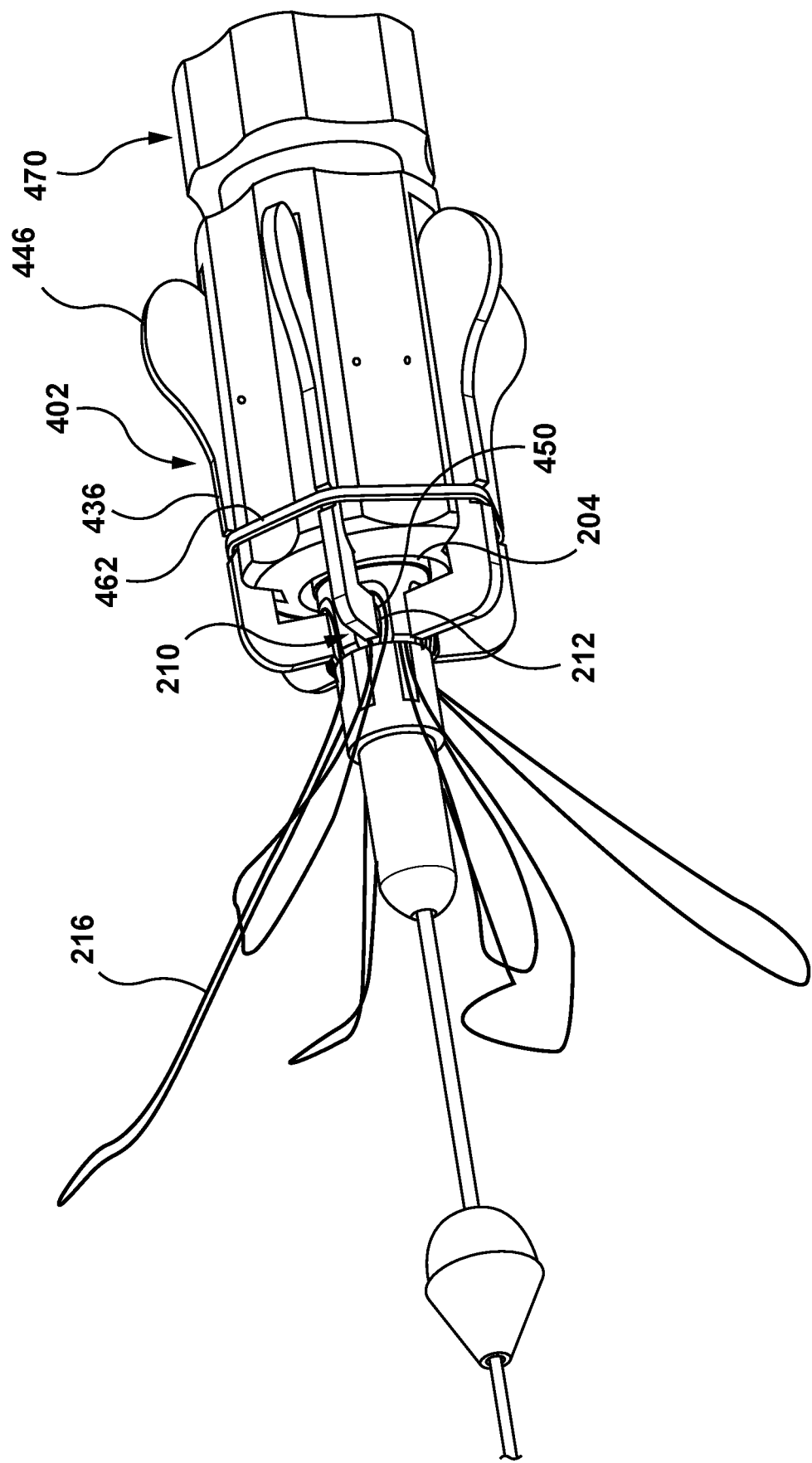
FIG. 20 is a perspective illustration of the loading tool of FIG. 15 on the delivery catheter of FIG. 6A with the tethers extended.

Referring to FIG. 20, the tool 402 is fitted over the distal portion of the delivery catheter 200. More specifically, the distal tip 206 of the delivery catheter 200 is placed into the proximal end 406 of the central passageway 410 of the loading tool 402, and the tool 402 is moved proximally over the distal portion of the delivery catheter 200. The loading tool 402 is positioned over the distal portion of the delivery catheter 200 (and more specifically the outer sheath 204) with each contact surface 450 of each pivotable element 436 of the loading tool 402 positioned with a distal end of the contact surface 450 aligned with a distal end of the corresponding tether post 212. The contact surface 450 of each pivotable element 436 is longitudinally aligned such that the contact surface 450 covers the corresponding tether post 212 and the corresponding groove 214. The loading tool 402 is aligned circumferentially such that the contact surface 450 of each pivotable element 436 is positioned along the longitudinal centerline of the corresponding tether post 212. As shown in FIG. 20, the distal end of the outer sheath 204 is proximal of the tether posts 212. The biasing element 462 of the loading tool 402 exerts inward radial on each pivotable element 436 inward toward the first longitudinal axis LA1 of the tool body portion 404 such that the contact surface 450 of each pivotable element 436 will remain in physical contact with the respective tether post 212.

Once the loading tool 402 is properly positioned correctly over the distal portion of the delivery catheter 200 with the contact surfaces 450 of the plurality of pivotable arms 436 disposed over and in contact with the corresponding tether post 212, the gripable portion 480 of the securing device 470 is rotated in a first direction such that the threads 498 (FIG. 19) of the securing device 470 engage with the corresponding threads 413 (FIG. 17) of the central passageway 410 (FIG. 17) to move (translate) the securing device 470 distally (in the direction of arrow 497, as shown in FIG. 20) within the central passageway 410 and relative to the body portion 404. The distal movement of the securing device 470 relative to the body portion 404 moves the plurality of fingers 492 of the securing device 470 distally further into the tapered portion 418. As the plurality of fingers 492 advance further distally into the tapered portion 418 of the central passageway 410, the decreasing diameter of the tapered portion 418 imparts an increasing inward radial force (pressure) on the plurality of fingers 492 disposed therein. The inward radial force (pressure) imparted by the wall of the central passageway 410 deforms the fingers 492 radially inward. With continued distal movement of the fingers 492 within the tapered portion 418 of the central passageway 410, the deformation of the fingers 492 increases until an inner surface of the plurality of fingers 492 contacts the outer surface of the outer sheath 204 disposed therein to releasably couple (grip or secure) the tool 402 to the outer shaft 204 of the delivery catheter 200. Securing the tool 402 to the delivery catheter 200 ensures that the tool 402 will not move during the securing of the tethers, described below, thereby enabling the user to use both hands to secure the tethers. Next, with the tool 402 releasably coupled to the outer sheath 204 of the delivery catheter 200 and the contact surface 450 of each pivotable element 436 in contact with the respective tether posts 212, the plurality of tethers 216 are extended by manipulation of the handle assembly 201 (not shown) to form large loops as shown in in FIG. 20.

Figure 21:
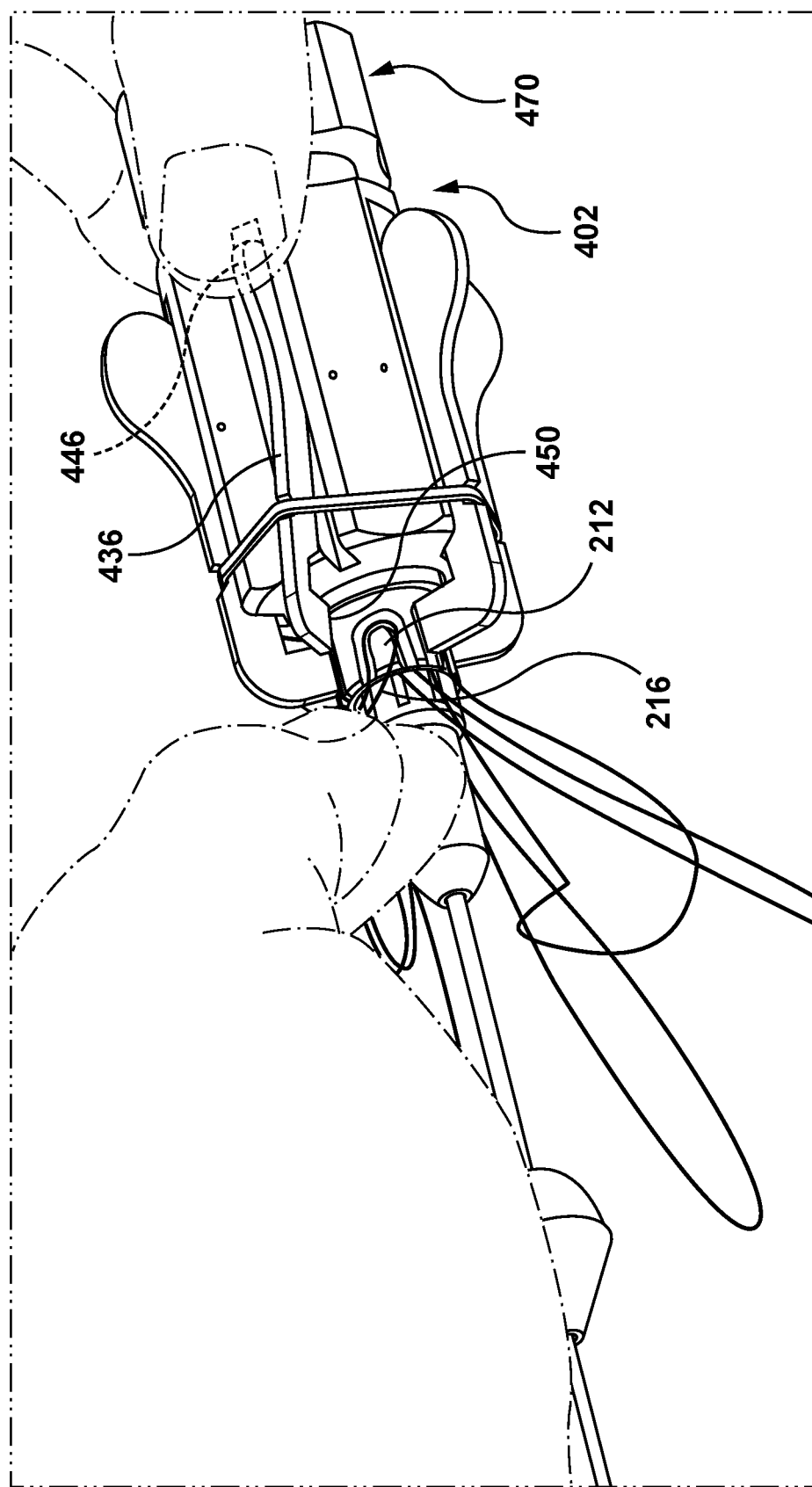
FIG. 21 is a perspective illustration of the loading tool of FIG. 15 on the delivery catheter of FIG. 6A showing a loop of a tether being disposed under a pivotable element of the loading tool.
Figure 22A:
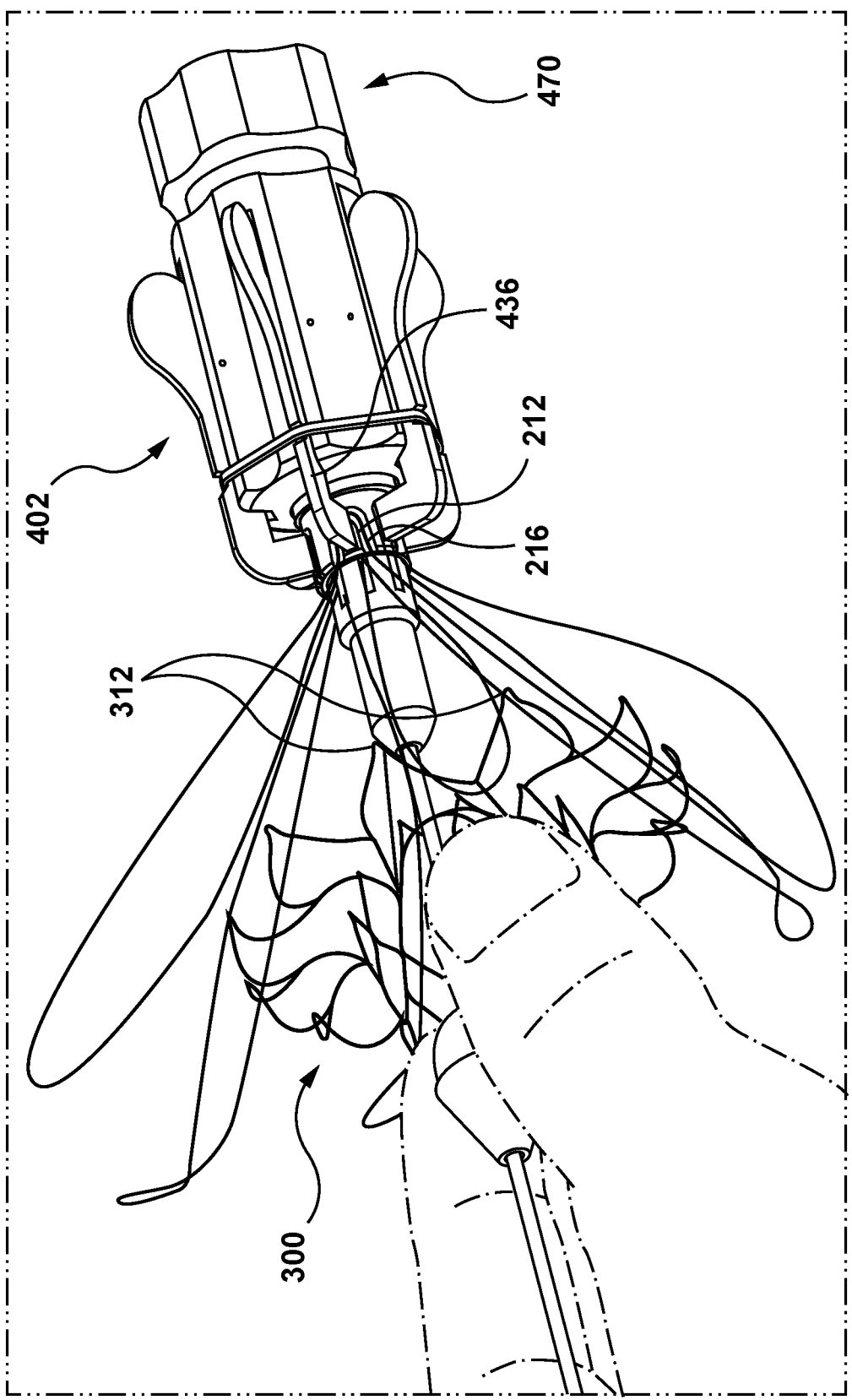
FIG. 22A is a perspective illustration of the delivery catheter of FIG. 6A with one of the tethers looped through the frame of the valve prosthesis of FIG. 7A and trapped by the loading tool of FIG. 15.
Figure 22B:
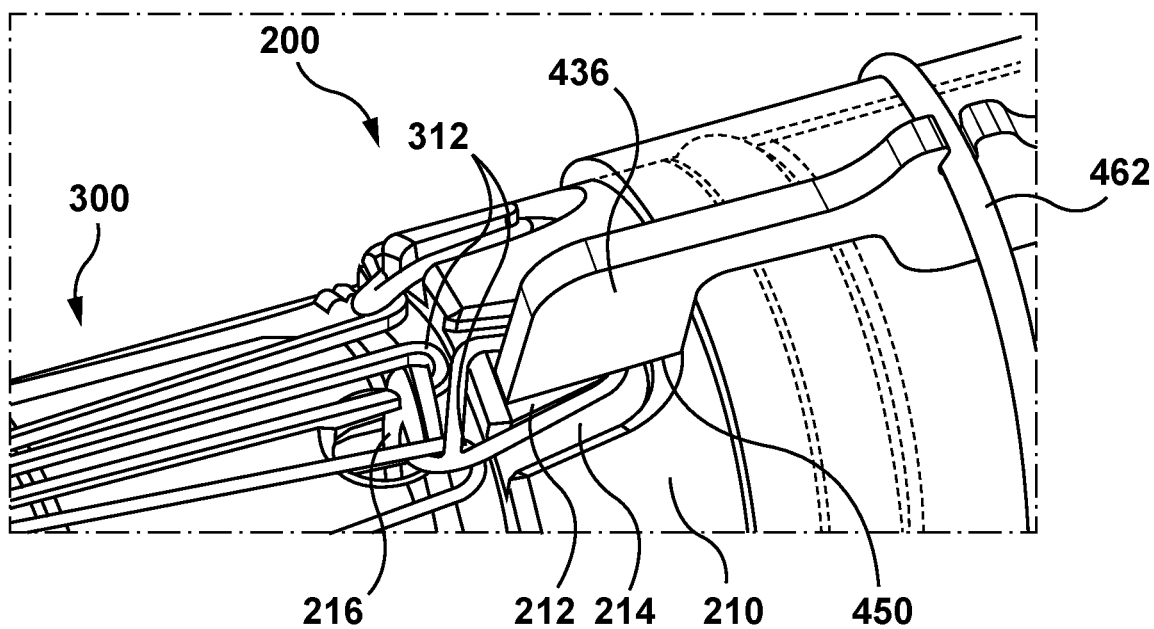
FIG. 22B is a closer perspective illustration of the delivery catheter of FIG. 6A with one the tethers looped through the frame of the valve prosthesis of FIG. 7A and trapped by the loading tool of FIG. 15.

Once the tethers 216 are in large loops, the valve prosthesis 300 is connected to the valve retainer 210 of the delivery catheter 200. FIG. 21 shows how each tether 216 is doubled back on itself and can be inserted into a groove 214 of a tether post 212 while the user presses on the actuating surface 446 of a pivotable element 436. FIG. 21 is shown without the valve prosthesis 300 for clarity. In practice, in an embodiment, each tether 216 is looped through or around two crowns 312 of the valve prosthesis 300. The user then actuates the corresponding pivotable element 436 to transition the pivotable element 436 from the first configuration to the second configuration. Once the pivotable element 436 is in the second configuration, the tether 216 is looped around the corresponding tether post 212 within the corresponding groove 214 thereof, as generally shown in FIGS. 22A-22B. When the respective tether 216 is looped around the tether post 212 and in the adjacent groove 214, the user deactuates the pivotable element 436. More specifically, the user-applied inward radial pressure (force) on the pivotable element 436 is removed. When the user actuated inward radial pressure (force) is removed, the biasing element 462 exerts an inward radial force on the distal portion of the pivotable element 436. The inward radial force from the biasing element 462 pivots the pivotable element 436 to the first (closed) configuration and the contact surface 450 contacts the tether post 212, covering the tether post 212 and the adjacent groove 214. When in contact with the tether post 212 and covering the groove 214, the contact surface 450 retains the corresponding tether 216 therein. This action is completed for each tether 216 and corresponding tether post 212 of the delivery catheter 200.

Once the plurality of tethers 216 looped around the corresponding tether posts 212 and are retained within the corresponding groove 214 by the respective pivotable elements 436, the gripable portion 480 of the securing device 470 is rotated in a second direction opposite the first direction. Rotation of the gripable portion 480 in the second direction moves the securing device 470 proximally with respect to the body portion 404 of the tool 402. More specifically, the plurality of fingers 492 of the securing device 470 move proximally within the tapered portion 418 of the central passageway 410 and the increasing diameter of the tapered portion 418 releases the inward radial force (pressure) on the plurality of fingers 492. The decreasing inward radial force (pressure) allows the plurality of fingers 492 (FIG. 19) to return to their original (undeformed) shape and the inner surface of the plurality of fingers 492 disengage from the outer surface of the outer sheath 204 to uncouple the tool 402 from the delivery catheter 200. However, the body portion 404 of the tool 402 remains in place such that the pivotable elements 436 retain the tethers 216 within the grooves 214 around the tether posts 212. The above-described loosening of the securing device 470 allows relative movement between the outer shaft 404 and the tool 402, but the tool 402 is held in place by the user.

Once the tethers 216 are secured around the tether posts 212 and the tool 402 has been loosened, the outer sheath 204 of the delivery catheter 200 is moved distally by manipulating the handle assembly 201 (not shown). As the outer sheath 204 advances distally, it will lift (slide under) each contact surface 450 (FIG. 22B) of each pivotable element 436, thereby covering the respective grooves 214 and tether posts 212 and retaining the tethers 216 therein. Each tether 216 is thus retained in the corresponding groove 214 and around the corresponding tether post 212 by an inner surface of the outer sheath 204, and the valve prosthesis 300 is releasably coupled to the delivery catheter 200, as shown in FIG. 23.

Figure 23:
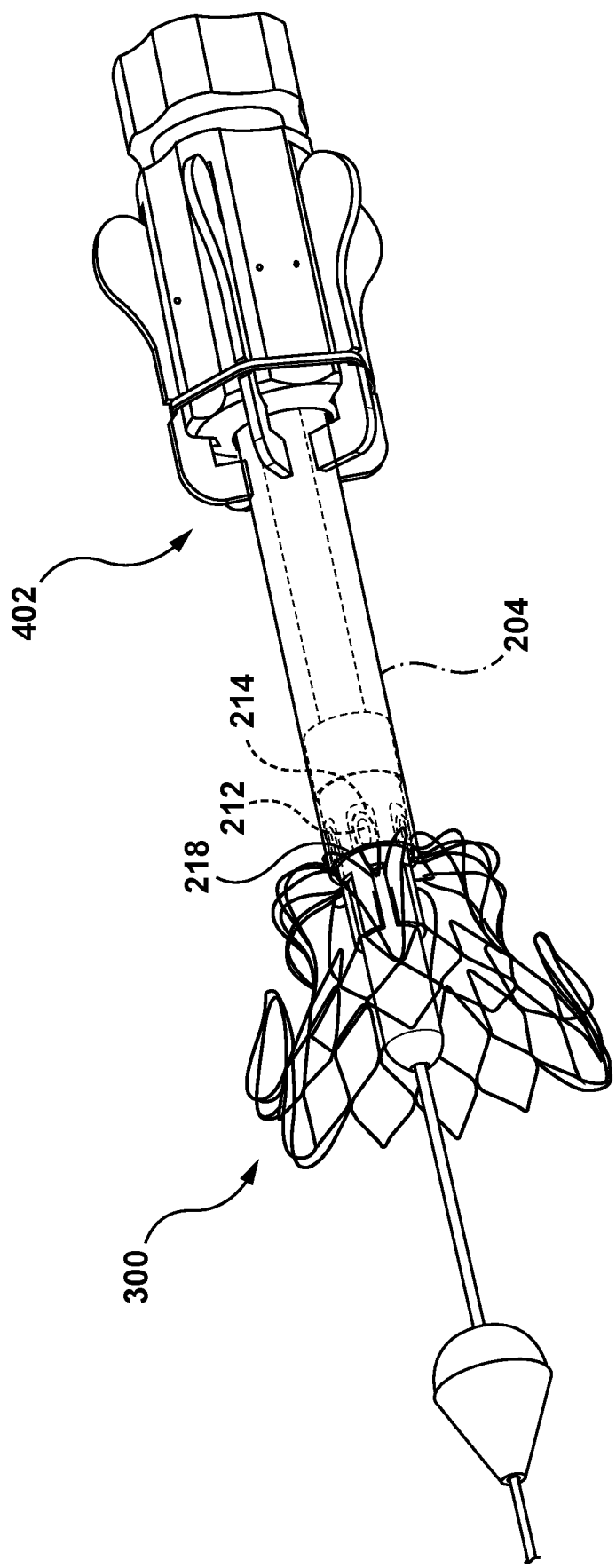
FIG. 23 is a perspective illustration of the plurality of tethers trapped by the outer sheath of delivery catheter of FIG. 6A.

With the valve prosthesis 300 releasably coupled to the delivery catheter 200, the tool 402 may be retracted proximally away from the distal end 218 of the outer sheath 204, as shown in FIG. 23. Also, the handle assembly 201 is manipulated by the user and the plurality of tethers 216 are retracted to remove slack, as shown in FIG. 23.

Figure 24A:
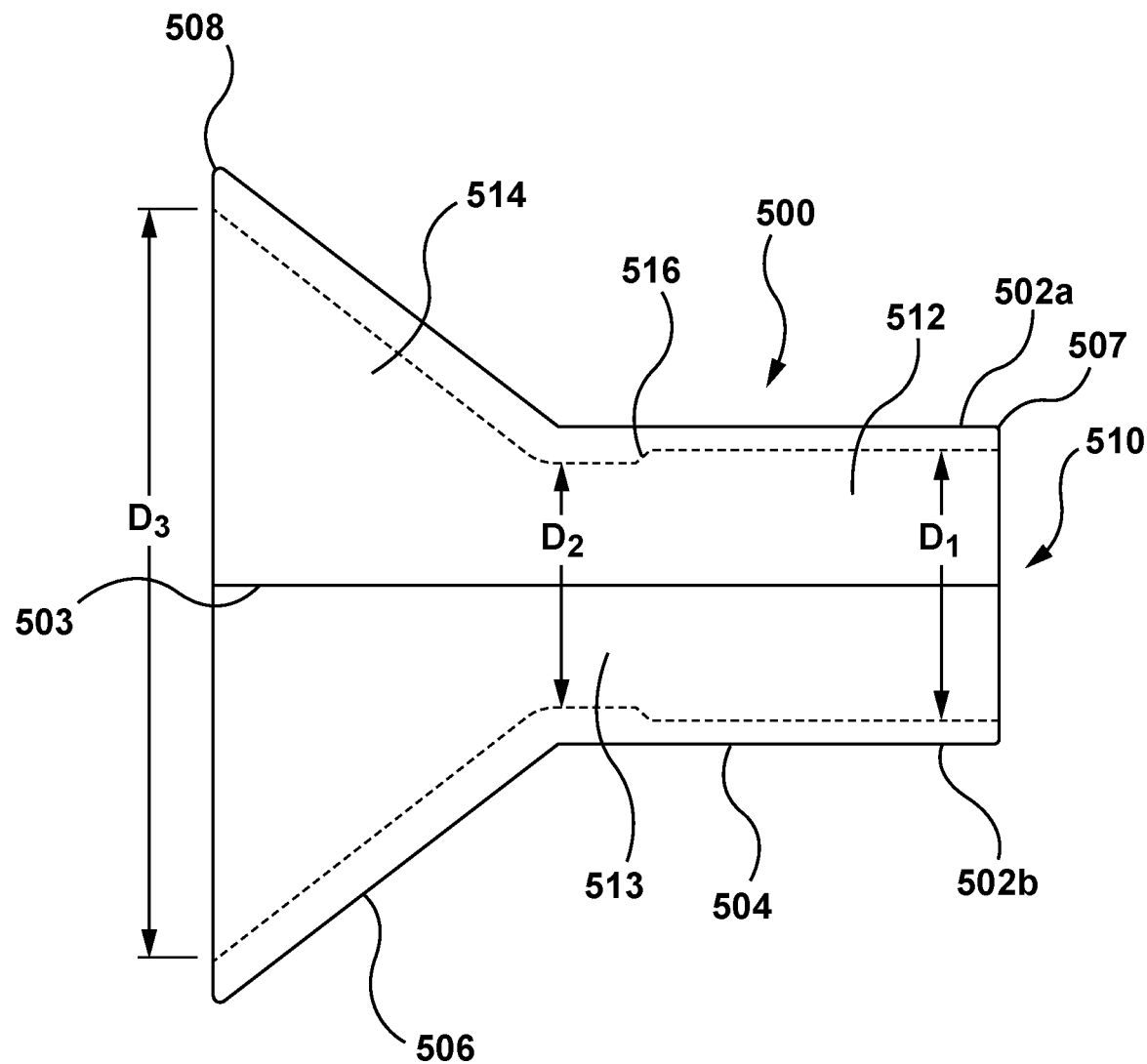
FIG. 24A is a side illustration of loading cone in accordance with an embodiment hereof.
Figure 24B:
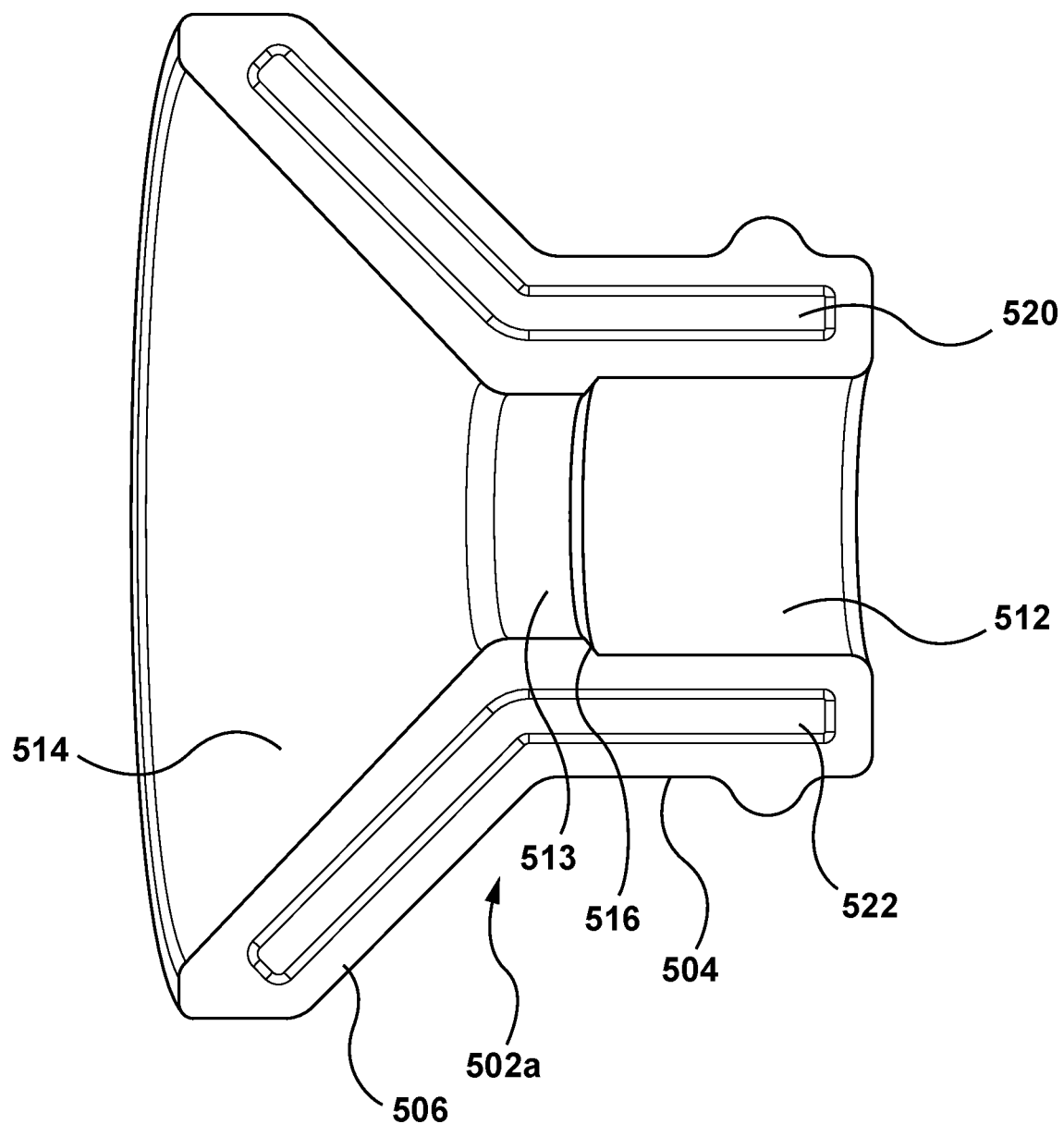
FIG. 24B is a side illustration of a portion of the loading cone of FIG. 24A.

A loading cone 500 may next be positioned over the outer sheath 204 near the distal end 218. The loading cone 500 is shown in FIGS. 24A and 24B. In an embodiment, the loading cone 500 includes a first body portion 502*a* and a second body portion 502*b* configured to be coupled to each other. The first and second body portions 502*a*, 502*b* are split along a longitudinal parting line 502, as shown in FIG. 24A. The first and second body portions 502*a*, 502*b* may be coupled together by matching up circumferential edges 520, 522 of each (see FIG. 24B). The edges 520, 522 may include features to couple the first and second body portions 502*a*, 502*b* together, such as, but not limited to, a protrusion in one of the edges of one of the body portions and a corresponding groove in the corresponding edge of the other body portion.

The loading cone 500 includes a proximal end 507 and a distal end 508. The loading cone further includes a first, generally cylindrical portion 504 and a second, generally frustoconical portion 506. The loading cone further includes a central passageway 510 extending from the proximal end 507 to the distal end 508, as shown by the dotted lines in FIG. 24A. The central passageway 510 includes a proximal portion 512, a central portion 513, and a distal, flaring portion 514. The proximal portion 512 has a generally consistent first diameter D1 extend from the proximal end 507 of the loading cone 500 to a location adjacent but proximal of the second portion 506 of the loading cone 500. The central portion 513 of the central passageway 510 begins at a shoulder 516 that reduces the diameter of the central passageway from the first diameter D1 to a second diameter D2. As explained in more detail below, when the loading cone is secured to the outer shaft 204 of the delivery catheter 200, the outer sheath 204 is disposed in the proximal portion 512 of the central passageway 510 with the distal end 218 of the outer shaft 204 is disposed against or abutting the shoulder 516. The distal portion 514 of the central passageway 510 extends from a proximal end co-located with a distal end of the central portion 513, and flares outwardly to a distal end at the distal end 508 of the loading cone 500. The distal portion 514 of the central passageway flares from the second diameter D2 to a third diameter D3 that is larger than the second diameter D2 and larger than the first diameter D2. Although a specific embodiment of a loading cone has been described above, other loading cones may be utilized in keeping with the purposes described herein.

Figure 25A:
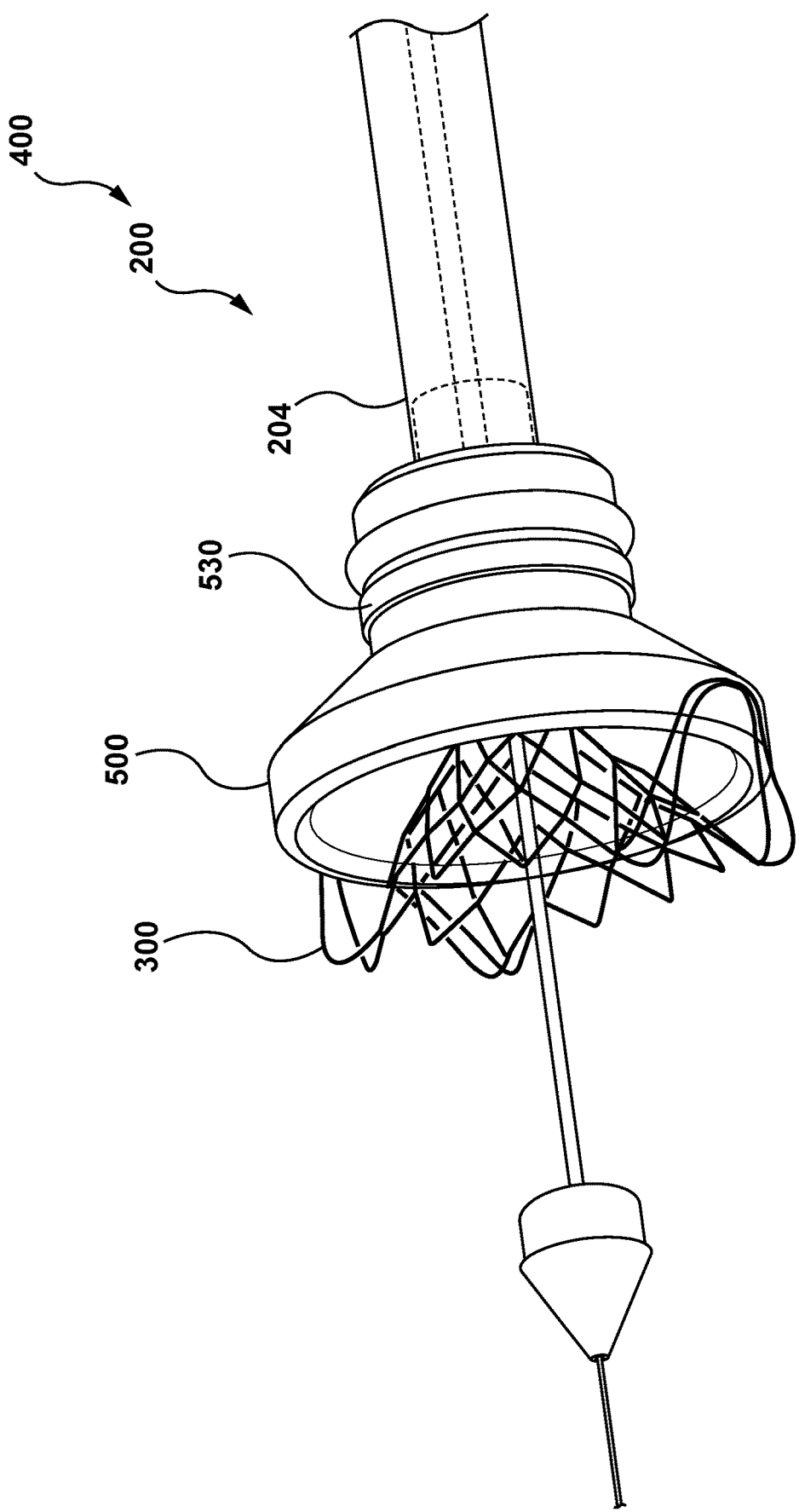
FIGS. 25A-25E are perspective illustrations of the loading of the valve prosthesis of FIG. 7A into a capsule of the delivery catheter of FIG. 6A with the loading cone of FIG. 24A.
Figure 25B:
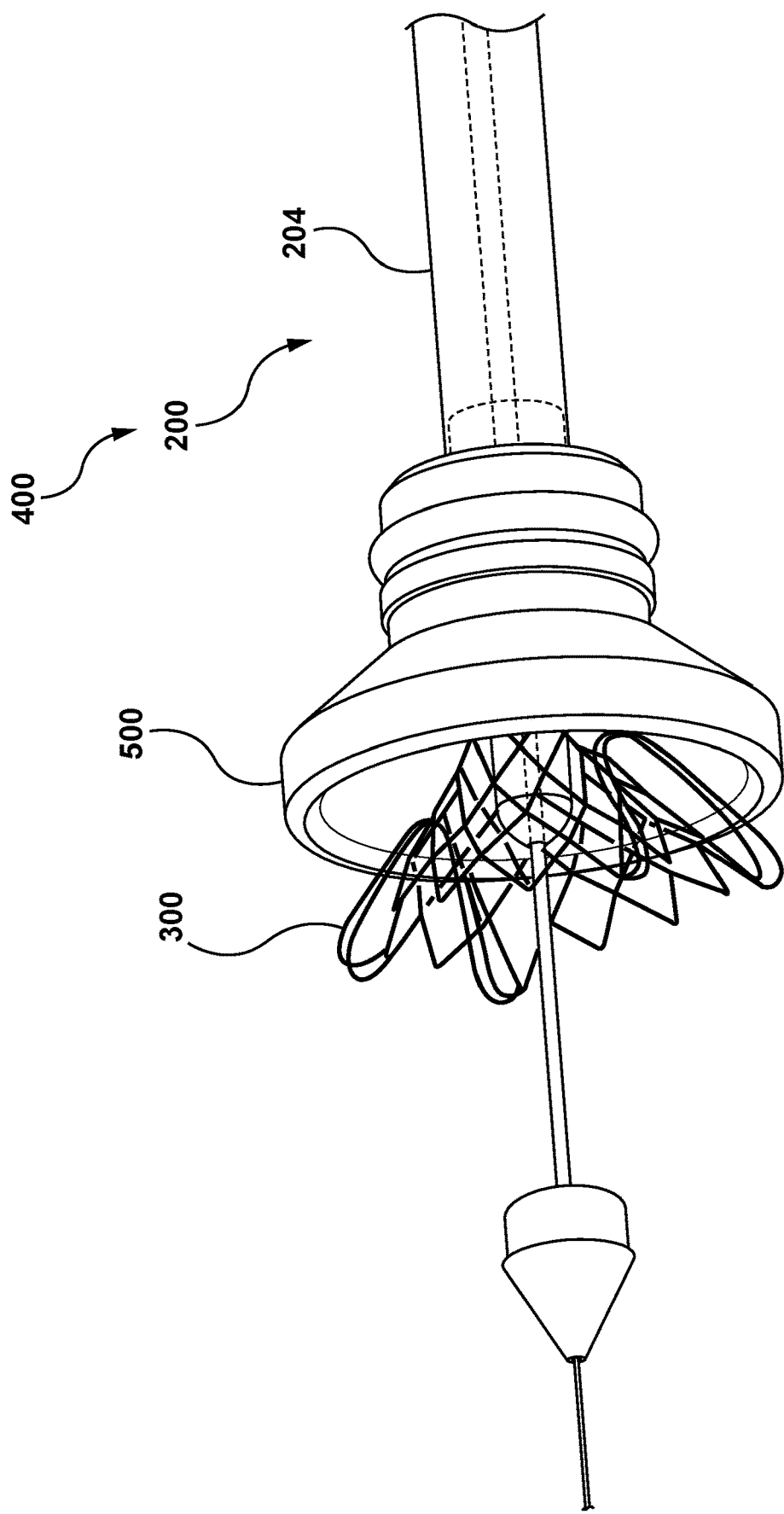
Figure 25C:
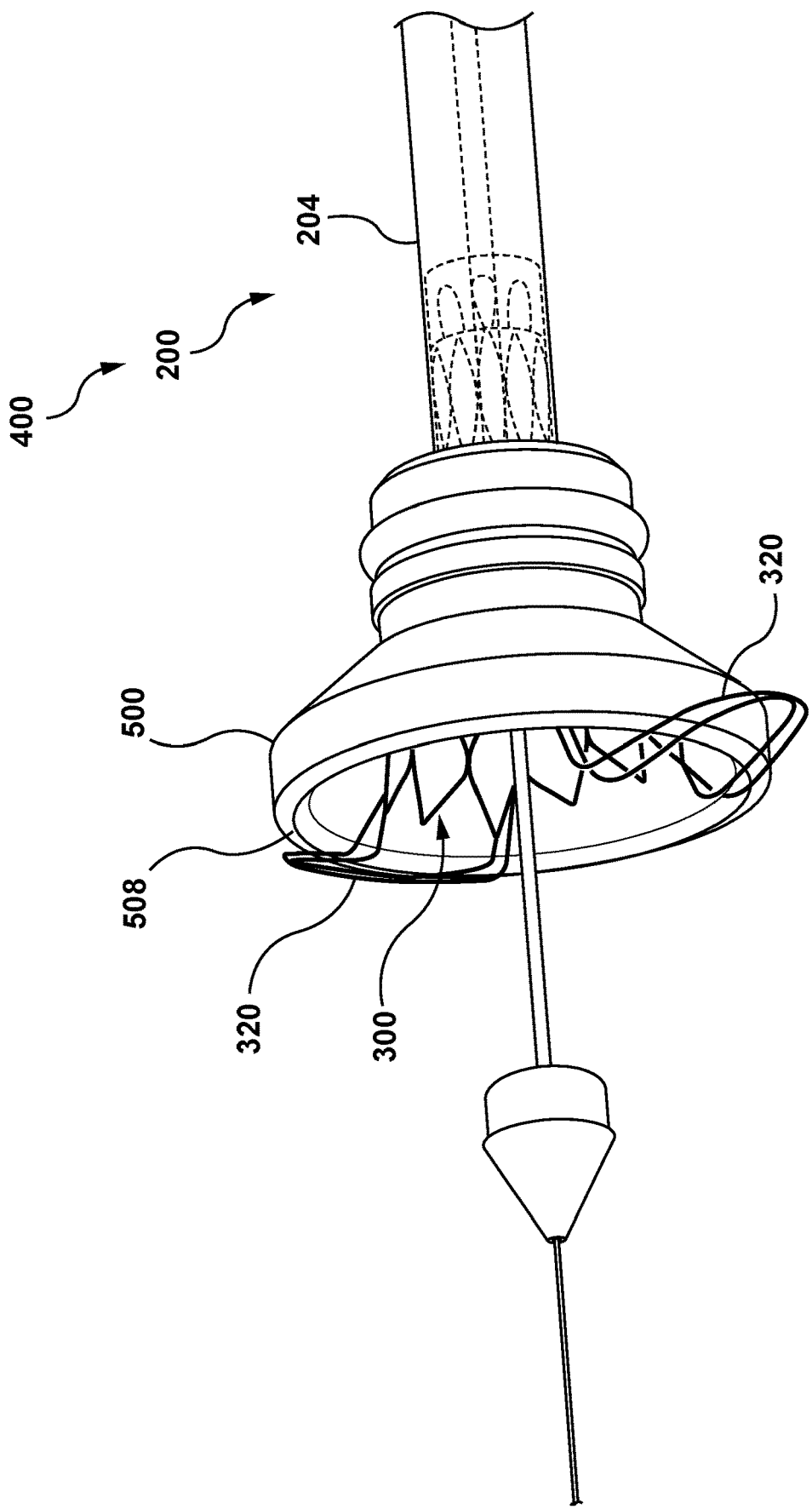
Figure 25D:
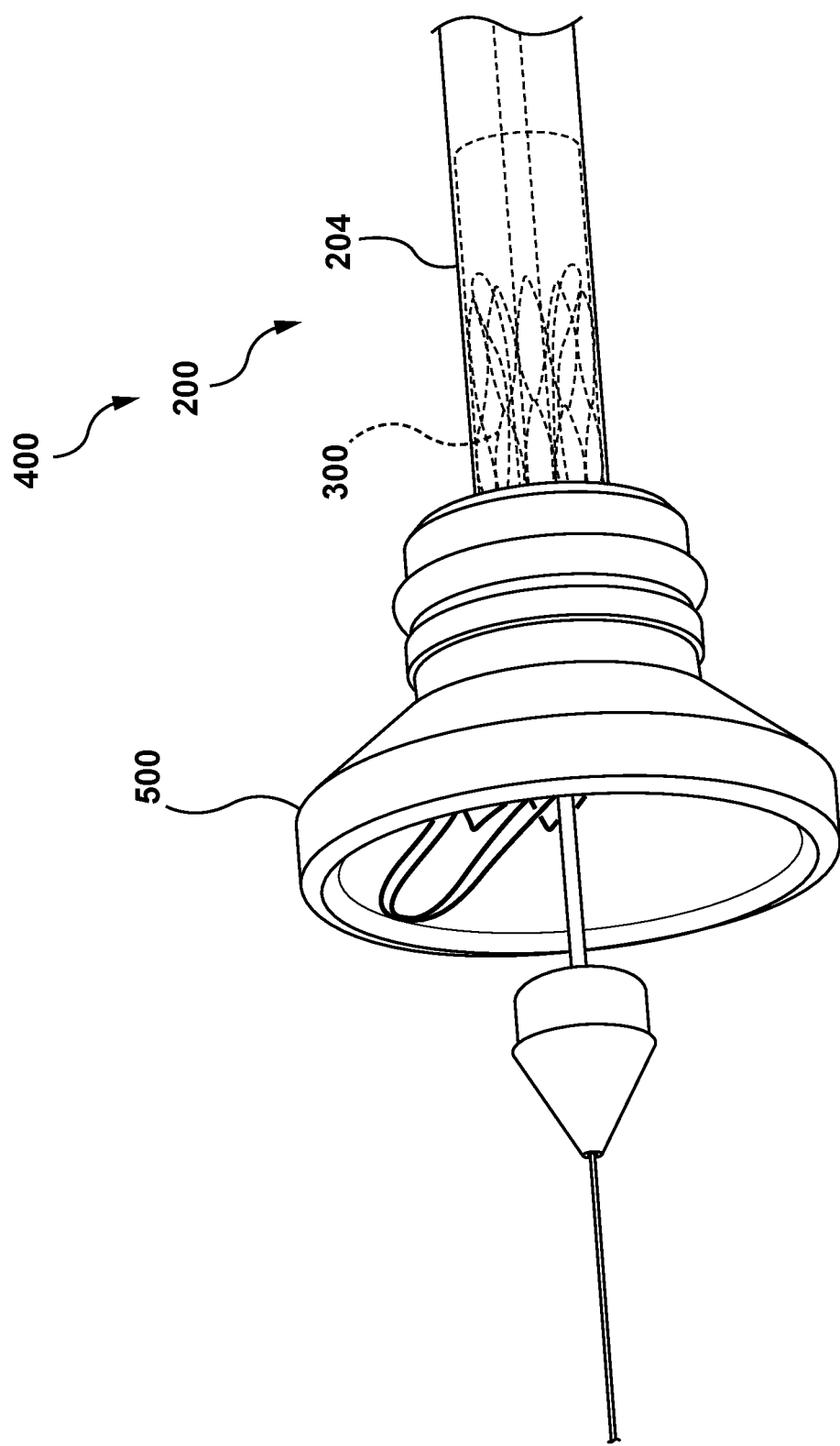
Figure 25E:
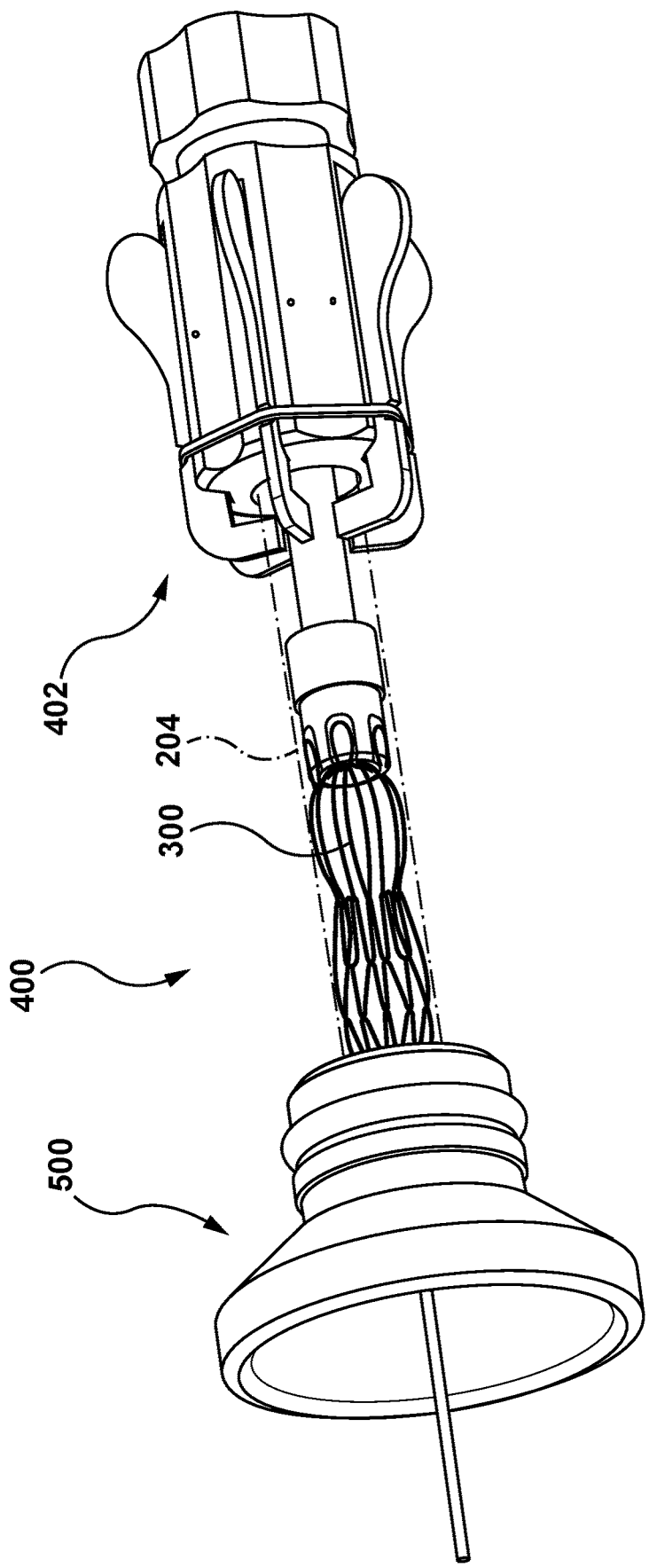

The loading cone 500 is split along the parting line 503 and placed around the outer sheath 204. The loading cone 500 is located such that the outer sheath 204 is disposed in the proximal portion 512 of the central passageway 510 and the distal end 418 of the outer sheath abutting against the shoulder 516. A zip tie 530 or similar securing device may be used to securely couple the loading cone to the outer sheath 204, as shown in FIG. 25A. With the loading cone 500 secured to the outer sheath 204 as described, the outer sheath 204 is advanced distally by manipulation of the handle assembly 201. As the outer sheath 204 is advanced, the distal end 418 of the outer sheath 204 pushes against the shoulder 516 of the loading cone 500, thereby advancing the loading cone 500 with the outer sheath 204. As the outer sheath 204 and loading cone 500 are advanced, the valve prosthesis 300 is radially collapsed within the distally advancing outer sheath 204. The loading cone 500 assists in radially collapsing the valve prosthesis 300. FIGS. 25A-25E illustrate the slow radial collapse and loading (movement) of the valve prosthesis 300 into the outer sheath 204 of the delivery catheter 200 of the system 400. If the valve prosthesis includes arms 320, as shown, the arms 320 may be situated such that the distal end 508 of the loading cone 500 everts the arms 320 as the outer sheath 204 and the loading cone 500 are advanced, as shown in FIG. 25C-25E.

Figure 26:
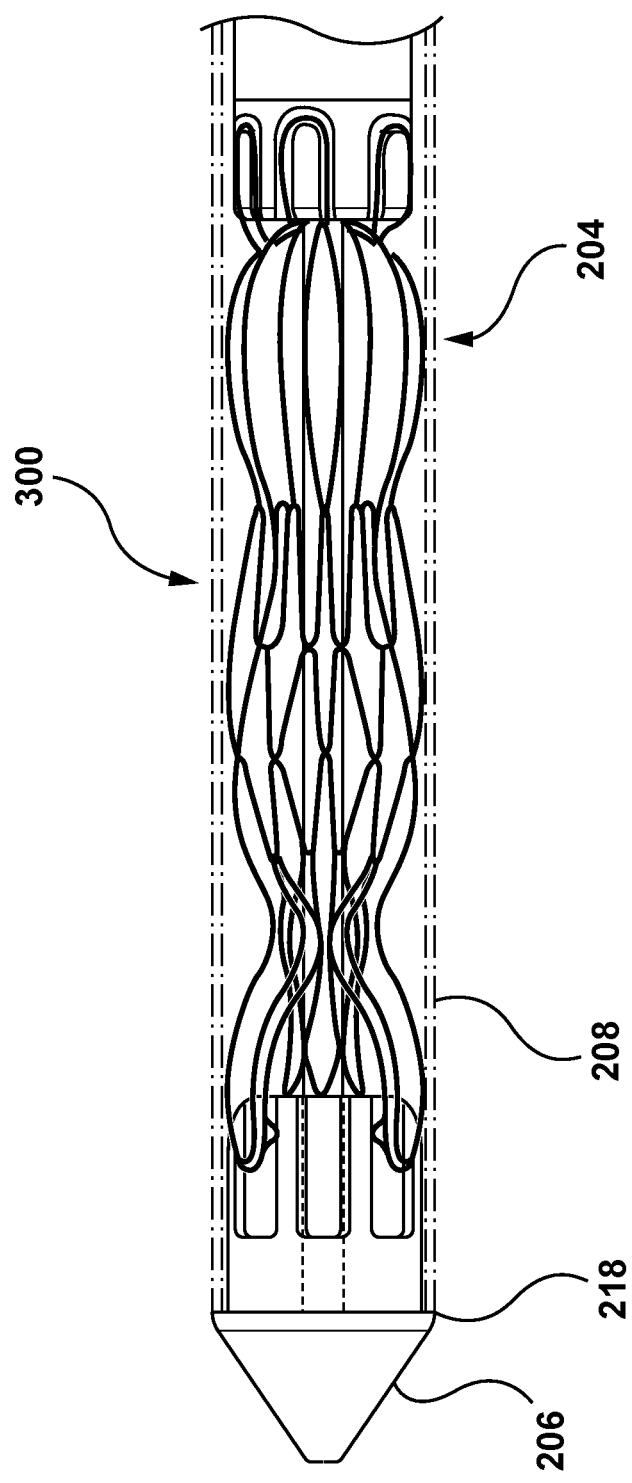
FIG. 26 is a perspective illustration of the loaded capsule of the delivery catheter of FIG. 6A.

With the valve prosthesis 300 fully retained within the capsule 208 of the delivery catheter 200, the outer sheath 204 is advanced until the distal end 218 contacts the proximal end of the distal tip 206. The compressed valve prosthesis 300 is now retained within the capsule 208 of the delivery catheter 200, as shown in FIG. 26. The loading cone 500 is then removed. Finally, the loading tool 402 may now be removed from the delivery catheter 200 by sliding it distally off the distal end of the delivery catheter 200.

While the present disclosure is directed to a system, including a loading tool ("tool") for loading a valve prosthesis (stented transcatheter prosthetic heart valve) into a delivery catheter with tethers, the loading tools disclosed herein are not limited for use with the valve prostheses described herein or limited for use with delivery catheters with tethers. For example, and not by way of limitation, the loading tools disclosed herein may be useful for assisting in loading other valve prostheses, stented prosthetic heart valves, stents, stent-grafts, and other similar devices into other delivery catheters. Further, rather than trapping tethers of the delivery catheter, as described above, the loading tools described herein may trap other items, such as, but not limited to, crowns of valve prostheses.

While only some embodiments of systems, devices and methods have been described herein, it should be understood that it has been presented by way of illustration and example only, and not limitation. Various changes in form and detail can be made therein without departing from the spirit and scope of the invention. Each feature of each embodiment discussed herein, and each reference cited herein, can be used in combination with the features of any other embodiment. All patents and publications discussed herein are incorporated by reference herein in their entirety.

What is claimed is:

1. A method of loading a valve prosthesis into a delivery catheter comprising:
   locating a tool at a distal portion of an outer sheath of the delivery catheter adjacent a valve retainer of the delivery catheter;
   extending a tether of the delivery catheter through a portion of the valve prosthesis and to the valve retainer; and
   moving a pivotable element of the tool such that a contact surface of the pivotable element maintains the tether in contact with the valve retainer; and
   wherein the delivery catheter includes a plurality of tethers and the tool includes a plurality of pivotable elements, wherein each of the plurality of tethers is extended through a corresponding portion of the valve prosthesis, and wherein each of the plurality of pivotable elements is moved such that a contact surface of the pivotable elements maintains a corresponding one of the plurality of tethers in contact with the valve retainer.

2. The method of claim 1, further comprising: removing slack in the tethers.

3. The method of claim 1, further comprising: after moving the pivotable elements so as to maintain the tethers in contact with the valve retainer, advancing the outer sheath between the tethers and the contact surfaces of the pivotable elements such that the outer sheath maintains the tethers in contact with the valve retainer.

4. The method of claim 3, further comprising:
   after advancing the outer sheath between the tethers and the contact surfaces, removing the tool from the tool from the delivery catheter.

5. The method of claim 4, wherein the tool includes a central passageway with a tapered portion, further comprising:
   after advancing the outer sheath between the tethers and the contact surfaces, advancing the tool and the outer sheath over the valve prosthesis such that the tapered portion of the central passageway of the tool radially collapses the valve prosthesis.

6. The method of claim 1,
   wherein the valve retainer includes a groove and a tether post,
   wherein extending the tether to the valve retainer includes placing the tether within the groove of the valve retainer, and
   wherein moving the pivotable element of the tool such that a contact surface of the pivotable element maintains the tether in contact with the valve retainer comprises moving the pivotable element into contact with the tether post to maintain the tether in the groove.

7. The method of claim 1,
   wherein locating the tool at a distal portion of an outer sheath of the delivery catheter adjacent the valve retainer of the delivery catheter includes locating the tool such that the contact surface of the pivotable element in in contact the valve retainer, and
   wherein prior to or during extending the tether to the valve retainer, the pivotable element is moved such that the tether is advanced between the contact surface and the valve retainer.

8. The method of claim 1,
   wherein the tool includes a biasing element that compresses the pivotable element against a body portion of the tool, and wherein moving the pivotable element of the tool comprises pressing a first end of the pivotable element opposite a second end of the pivotable element including the contact surface such that a biasing force of the biasing element in overcome.

9. The method of claim 1, wherein the pivotable element includes a first configuration with the contact surface of the pivotable element in contact with the valve retainer and a second configuration with the contact surface radially spaced from the valve retainer.

10. The method of claim 9, wherein the tool includes a biasing element that biases the pivotable element to the first configuration, and wherein moving the pivotable element to the second configuration comprises pressing a first end of the pivotable element opposite a second end of the pivotable element including the contact surface such that a biasing force of the biasing element is overcome.

11. The method of claim 10, wherein the tool includes a third configuration in which the pivotable element is maintained radially spaced from the valve retainer without a user pressing the pivotable element.

12. The method of claim 11, wherein the pivotable element includes a pin that extends through a slot in the pivotable element, wherein the slot extends generally parallel to the longitudinal axis of the tool when the pivotable element is in the second configuration such that the pivotable element is distally slidable along the pin relative to a body portion of the tool to move the pivotable element from the second configuration to the third configuration.

13. A method of loading a valve prosthesis into a delivery catheter comprising:
   locating a tool at a distal portion of an outer sheath of the delivery catheter adjacent a valve retainer of the delivery catheter, wherein the tool includes a plurality of pivotable elements;
   extending a plurality of tethers of the delivery catheter through respective portions of the valve prosthesis and to the valve retainer;
   individually locating each tether of the plurality of tethers at a corresponding location of the valve retainer;
   individually moving each of the pivotable elements of the tool such that the contact surface of the each pivotable element maintains the corresponding tether in contact with the valve retainer.

14. The method of claim 13, further comprising:
after moving the pivotable elements so as to maintain the tethers in contact with the valve retainer, advancing the outer sheath between the tethers and the contact surfaces of the pivotable elements such that the outer sheath maintains the tethers in contact with the valve retainer.

15. The method of claim 13,
wherein the tool includes a biasing element that compresses each of the pivotable elements against a body portion of the tool, and wherein individually moving each of the pivotable elements of the tool comprises pressing a first end of each of the pivotable elements opposite a second end of the pivotable element including the contact surface such that a biasing force of the biasing element in overcome and the contact surface moves radially away from the contact surface to enable a corresponding tether to be located at the valve retainer and releasing the first end of each of the pivotable elements such that the biasing force returns the pivotable element towards the valve retainer to maintain the corresponding tether in contact with the valve retainer.

16. The method of claim 13, wherein each of the pivotable elements includes a first configuration with the contact surface of the pivotable element in contact with the valve retainer and a second configuration with the contact surface radially spaced from the valve retainer.

17. The method of claim 16, wherein the tool includes a biasing element that biases each of the pivotable elements to the first configuration, and wherein moving each of the pivotable elements to the second configuration comprises pressing a first end of the pivotable element opposite a second end of the pivotable element including the contact surface such that a biasing force of the biasing element in overcome.

18. The method of claim 17, wherein the tool includes a third configuration in which the pivotable element is maintained radially spaced from the valve retainer without a user pressing the pivotable element.

19. The method of claim 18, wherein each of the pivotable elements includes a pin that extends through a slot in the pivotable element, wherein the slot extends generally parallel to the longitudinal axis of the tool when the pivotable element is in the second configuration such that the pivotable element is distally slidable along the pin relative to a body portion of the tool to move the pivotable element from the second configuration to the third configuration.

* * * * *